(12) United States Patent
Jansson et al.

(10) Patent No.: US 12,168,089 B2
(45) Date of Patent: Dec. 17, 2024

(54) PERITONEAL DIALYSIS CYCLER HAVING HEAT CLEANING

(71) Applicants: BAXTER INTERNATIONAL INC., Deerfield, IL (US); BAXTER HEALTHCARE SA, Glattpark (CH)

(72) Inventors: Olof Jansson, Vellinge (SE); Mattias Holmer, Lund (SE)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 0 days.

(21) Appl. No.: 18/269,823

(22) PCT Filed: Dec. 16, 2021

(86) PCT No.: PCT/US2021/063816
§ 371 (c)(1),
(2) Date: Jun. 27, 2023

(87) PCT Pub. No.: WO2022/146706
PCT Pub. Date: Jul. 7, 2022

(65) Prior Publication Data
US 2023/0390471 A1    Dec. 7, 2023

Related U.S. Application Data

(60) Provisional application No. 63/131,442, filed on Dec. 29, 2020.

(51) Int. Cl.
*A61M 1/28* (2006.01)
*A61M 1/16* (2006.01)

(52) U.S. Cl.
CPC ............ *A61M 1/282* (2014.02); *A61M 1/166* (2014.02)

(58) Field of Classification Search
CPC .............. A61M 1/1686; A61M 1/1688; A61M 1/28–288; A61M 39/20
See application file for complete search history.

(56) References Cited

U.S. PATENT DOCUMENTS

| | | | | |
|---|---|---|---|---|
| 6,129,699 A | * | 10/2000 | Haight | A61M 5/14232 417/477.2 |
| 2001/0027289 A1 | | 10/2001 | Treu et al. | |

(Continued)

OTHER PUBLICATIONS

International Search Report for PCT/US2021/063816 dated Apr. 7, 2022—7 pages.

(Continued)

*Primary Examiner* — Kami A Bosworth
(74) *Attorney, Agent, or Firm* — K&L Gates LLP

(57) ABSTRACT

A peritoneal dialysis ("PD") system includes a dialysis fluid pump having a reusable pump body that accepts PD fluid for pumping; a dialysis fluid inline heater including a reusable heater body that accepts PD fluid for heating; a patient line connector; a drain line connector; a first reusable PD fluid line including a first connector configured to mate with the patient line connector; a second reusable PD fluid line including a second connector configured to mate with the drain line connector; and a control unit configured to run a heat cleaning (e.g., heat disinfection or heat sterilization) sequence after PD treatment, wherein the first connector of the first reusable PD fluid line is mated with the patient line connector, the second connector of the second reusable PD fluid line is mated with the drain line connector, and the dialysis fluid pump and perhaps the dialysis fluid inline heater are actuated.

10 Claims, 6 Drawing Sheets

(56) References Cited

U.S. PATENT DOCUMENTS

| | | | |
|---|---|---|---|
| 2008/0033371 A1* | 2/2008 | Updegraff | A61M 39/20 |
| | | | 604/263 |
| 2009/0012450 A1 | 1/2009 | Shah et al. | |
| 2017/0319770 A1* | 11/2017 | Fitzgerald | A61M 1/282 |
| 2018/0021500 A1 | 1/2018 | Gerber et al. | |

OTHER PUBLICATIONS

Written Opinion for PCT/US2021/063816 dated Apr. 7, 2022—10 pages.

* cited by examiner

PERITONEAL DIALYSIS CYCLER HAVING HEAT CLEANING

PRIORITY CLAIM

This application is a national phase entry of PCT Patent Application No. PCT/US2021/063816, filed on Dec. 16, 2021, which claims priority to and the benefit of U.S. Provisional Application No. 63/131,442, entitled "Peritoneal Dialysis Cycler Having Heat Cleaning", filed on Dec. 29, 2020, the entire contents of which are incorporated herein by reference and relied upon.

BACKGROUND

The present disclosure relates generally to medical fluid treatments and in particular to dialysis fluid treatments.

Due to various causes, a person's renal system can fail. Renal failure produces several physiological derangements. It is no longer possible to balance water and minerals or to excrete daily metabolic load. Toxic end products of metabolism, such as, urea, creatinine, uric acid and others, may accumulate in a patient's blood and tissue.

Reduced kidney function and, above all, kidney failure is treated with dialysis. Dialysis removes waste, toxins and excess water from the body that normal functioning kidneys would otherwise remove. Dialysis treatment for replacement of kidney functions is critical to many people because the treatment is lifesaving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment. The substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD, HF, and HDF treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that more frequent treatments remove more toxins and waste products and render less interdialytic fluid overload than a patient receiving less frequent but perhaps longer treatments. A patient receiving more frequent treatments does not experience as much of a down cycle (swings in fluids and toxins) as does an in-center patient, who has built-up two or three days' worth of toxins prior to a treatment. In certain areas, the closest dialysis center can be many miles from the patient's home, causing door-to-door treatment time to consume a large portion of the day. Treatments in centers close to the patient's home may also consume a large portion of the patient's day. HHD can take place overnight or during the day while the patient relaxes, works or is otherwise productive.

Another type of kidney failure therapy is peritoneal dialysis ("PD"), which infuses a dialysis solution, also called dialysis fluid, into a patient's peritoneal chamber via a catheter. The dialysis fluid is in contact with the peritoneal membrane in the patient's peritoneal chamber. Waste, toxins and excess water pass from the patient's bloodstream, through the capillaries in the peritoneal membrane, and into the dialysis fluid due to diffusion and osmosis, i.e., an osmotic gradient occurs across the membrane. An osmotic agent in the PD dialysis fluid provides the osmotic gradient. Used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment. Here, the patient manually connects an implanted catheter to a drain to allow used or spent dialysis fluid to drain from the peritoneal chamber. The patient then switches fluid communication so that the patient catheter communicates with a bag of fresh dialysis fluid to infuse the fresh dialysis fluid through the catheter and into the patient. The patient disconnects the catheter from the fresh dialysis fluid bag and allows the dialysis fluid to dwell within the peritoneal chamber, wherein the transfer of waste, toxins and excess water takes place. After a dwell period, the patient repeats the manual dialysis procedure, for example, four times per day. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal chamber. APD machines also allow for the dialysis fluid to dwell within the chamber and for the transfer of waste, toxins and excess water to take place. The source may include multiple liters of dialysis fluid including several solution bags.

APD machines pump used or spent dialysate from the patient's peritoneal cavity, though the catheter, to drain. As with the manual process, several drain, fill and dwell cycles occur during dialysis. A "last fill" may occur at the end of the APD treatment. The last fill fluid may remain in the peritoneal chamber of the patient until the start of the next treatment, or may be manually emptied at some point during the day.

In any of the above modalities using an automated machine, the automated machine operates typically with a disposable set, which is discarded after a single use. Depending on the complexity of the disposable set, the cost of using one set per day may become significant. Also, daily disposables require space for storage, which can become a nuisance for home owners and businesses. Moreover, daily disposable replacement requires daily setup time and effort by the patient or caregiver at home or at a clinic.

For each of the above reasons, it is desirable to provide an APD machine that reduces disposable waste.

SUMMARY

Known automated peritoneal dialysis ("PD") systems typically include a machine or cycler that accepts and actuates a pumping cassette having a hard part and a soft part that is deformable for performing pumping and valving operations. The hard part is attached to tubes that extend to various bags. The disposable cassette and associated tubes and bags can be cumbersome for a patient at home to load for treatment. The overall number of disposable items may also lead to multiple setup procedures requiring input from the patient, which can expose room for error.

The APD system and associated methodology of the present disclosure, on the other hand, converts much of the fluid carrying portions of its APD system into reusable components, which are heat cleaned after treatment. Fluid lines within the machine or cycler are reused. Disposable items remaining may include the patient and drain lines, the dialysis fluid containers or bags and perhaps an additional dialysis fluid container and a tube or line extending from the container to the APD cycler.

The APD system of the present disclosure incudes an APD cycler having a housing. At least one and perhaps three or more reusable PD fluid lines extend from the housing. In one embodiment, when not connected to PD fluid containers or bags, the reusable PD fluid lines are connected to a patient line cycler connector, a drain line cycler connector and an additional cycler connector, which may be used to connect a fourth dialysis fluid container or bag to the cycler.

In another embodiment, when not connected to PD fluid containers or bags, the reusable PD fluid lines are connected to dedicated heat cleaning connectors. In either embodiment, the reconnected PD fluid lines form a closed loop, which allows for heat cleaning after treatment. It is contemplated to use leftover dialysis fluid as the heat cleaning fluid and to heat the same to a disinfection temperature, e.g., between 70° C. and 130° C., e.g., 70° C. for disinfection or 120° C. and above for sterilization.

The reusable PD fluid lines may be color coded and/or keyed to match a colored or keyed connector of the PD fluid container or bag. The containers or bags may hold different dextrose or glucose level dialysis fluids, such as 1.36% glucose dialysis fluid, 2.27% glucose dialysis fluid and/or a last bag of a different formulation of PD fluid, such as icodextrin.

Inside the housing, reusable tubing in a first primary embodiment runs from each of the reusable dialysis fluid lines, through a dialysis fluid line valve for each dialysis fluid line to a dialysis fluid inline heater. In an embodiment, any of the valves of the APD cycler may be an electrically actuated solenoid valve having a reusable valve body that closes (e.g., when unpowered) or opens to allow (e.g., when powered) PD fluid to flow through the body. Bi-stable valves may be used alternatively. The dialysis fluid inline heater is also electrically actuated in one embodiment and is, for example, a resistive heater having a reusable heater body that accepts PD fluid for heating. The inline heater in an embodiment is able to heat PD fluid from room temperature to body temperature, e.g., 37° C., at a flowrate of at least 300 milliliters ("ml")/minute. A temperature sensor is located adjacent to the heater, e.g., downstream from the heater, to provide feedback for temperature control.

Reusable tubing runs from the outlet of the dialysis fluid inline heater to a flowmeter dedicated for draining used dialysis fluid. Any of the tubing inside the housing of the cycler may be metal, e.g., stainless steel, or plastic, e.g., polyether ether ketone ("PEEK"), polyvinylchloride ("PVC") or a non-PVC material, such as polyethylene ("PE"), polyurethane ("PU") or polycarbonate ("PC"). A reusable dialysis fluid pump is located between the dedicated drain flowmeter and a dedicated fill flowmeter, which measures fresh dialysis fluid flow to the patient. The reusable pump includes a reusable pump body that accepts PD fluid for pumping. That is, the pump does not require the PD fluid to flow within a disposable item, such as a tube or cassette. The PD fluid pump may be an electrically operated piston, membrane, gear pump or centrifugal pump, which may be inherently volumetrically accurate so that a separate PD fluid volume measurement apparatus, such as a balance chamber or an apparatus using the ideal gas law, is not needed. The provision of the fill and drain flowmeters allows for a less accurate reusable PD fluid pump, such as a gear pump, centrifugal or other type of pump. In any case, the PD fluid pump may be controllable to pump to and from the patient at or below a pressure limit by controlling a level of current, voltage, or voltage pulse train to the PD fluid pump. A positive patient pressure limit may for example be one to five psig. A negative pressure limit may for example be −1.5 psig to −3.0 psig. The PD fluid pump is bidirectional and continuous in one embodiment, such that a single pump may be provided.

The first primary embodiment incudes an air trap in one embodiment, which may be located in different places along the main dialysis fluid or pumping line. In one implementation, the air trap is located between the dedicated fill flowmeter and the reusable PD fluid pump. A vent valve may be provided on the top of the air trap, which vents air from the air trap to drain. In an embodiment, one or more level sensor is located adjacent the air trap so that a desired level or range of levels of PD fluid may be maintained in the air trap.

A pressure sensor for the first primary embodiment is located downstream from the dedicated fill flowmeter, between the fill flowmeter and a disposable patient line. The disposable patient line connects to a patient connector provided by the housing of the cycler. Durable, reusable tubing runs from the patient connector along a line inside the housing to the dedicated fill flowmeter. The pressure sensor may be located along this line and outputs positive and negative patient pumping pressure signals, which are used to ensure that patient pumping pressure limits are not exceeded. One or more sterilizing filter may be located in the disposable patient line to provide a final stage of PD fluid filtration prior to delivery to the patient. The PD filter can for example be a pass-through filter that does not have a reject line. Pore sizes for the sterilizing filter may, for example, be less than a micron, such as 0.1 or 0.2 micron.

The drain line is also disposable in one embodiment and connects to a drain line connector extending from the housing of the APD cycler during treatment. Besides the valves provided for each of the dialysis fluid lines and the vent valve, additional valves may be provided upstream of the inline heater, adjacent to the patient line connector, adjacent to the drain line connector and adjacent to the additional connector used to connect a fourth dialysis fluid container or bag to the cycler.

After treatment, the patient line, drain line and the line connected to the additional connector are removed and discarded. The PD fluid containers or bags are removed from the reusable PD fluid lines. The reusable PD fluid lines are then reconnected to the patient line connector, drain line connector and the additional connector. The APD cycler and the reusable PD fluid lines are now fluidically closed, such that a heat cleaning fluid, such as heated fresh PD fluid may be pumped via the pump, in one or more direction, multiple times through the closed heat cleaning circuit to heat clean (e.g., heat disinfect or heat sterilize) the internal lines, the internal components (heater, air trap, pump, flowmeters, valves, etc.) and the reusable PD fluid lines for the next treatment.

The APD cycler of the APD system of the present disclosure includes a control unit having one or more processor and one or more memory that receive signals or outputs from the flowmeters, one or more pressure sensor, and one or more temperature sensor process the signals or outputs as feedback. The control unit uses pressure feedback to control the dialysis fluid pump to run at safe patient pressure limits during treatment and safe system limits during heat cleaning. The control unit uses temperature feedback to control the dialysis fluid heater to heat the fresh dialysis fluid to, e.g., body temperature. The control unit may also integrate the flowmeter signals to determine an overall amount of fresh PD fluid delivered to the patient and used PD fluid removed from the patient. Those amounts may be compared to determine an overall amount of ultrafiltration ("UF") removed from the patient.

The control unit also opens and closes the dialysis fluid valves in combination with the dialysis fluid pump and heater to run a priming sequence, a patient fill sequence, a patient drain sequence and a heat cleaning (e.g., heat disinfection or heat sterilization) sequence after a PD treatment, wherein each of the at least one reusable PD fluid line is connected to one of the line connectors as discussed above. The control unit just described is provided for each of the alternative primary embodiments discussed herein.

In a second primary embodiment, the reusable PD fluid lines are not plugged into the patient line and drain line connectors and are instead plugged into their own dedicated connectors for heat cleaning. The patient line and drain line connectors are provided instead with dedicated recirculation caps, which are fitted to the connectors after treatment for heat cleaning. The second primary embodiment replaces the flowmeters of the first primary embodiment with a highly inherently volumetrically accurate piston pump. The accuracy of the piston pump may be checked using the dialysis fluid inline heater. Here, at the start of each patient fill, a first few milliliters of fresh PD fluid are pumped through the heater without heating the fluid. A first temperature measurement T1 is taken. The heater is turned on and the effect needed to raise the temperature to T2, e.g., the filling temperature of 37° C., provides a measurement of PD fluid flow. That is, the specific heat capacity for water is known as is the temperature delta (T2−T1), which the control unit of the system uses to convert heating effect (energy/time) to flowrate (mass/time). If the difference between what the control unit calculates the fluid pump to have pumped and the value determined via the heater is outside of a limit, then the fluid pump is recalibrated.

A third primary embodiment, like the second primary embodiment, provides dedicated connectors for the reusable PD fluid lines, recirculation caps for the patient and drain line connectors and a highly accurate piston pump. The third primary embodiment separates the internal reusable lines within the housing of the cycler into PD fluid lines and operating fluid lines, wherein the operating fluid lines are filled with a different operating fluid, such as reverse osmosis ("RO") water. The RO water can also be used advantageously as a flush flow for the piston pump.

The PD fluid lines and operating fluid lines are separated by flexible membranes provided within a pair of balance chambers. Operating fluid drives one side of each of the balance chambers in a loop that includes the piston pump and an air trap for ensuring that there is enough operating fluid for each stroke. In each stroke, the RO pump (i) pulls RO water from one balance chamber, causing a like volume of fresh or used dialysis fluid to enter that balance chamber on the other side of the flexible membrane and (ii) delivers that RO water to the other balance chamber, causing a like volume of fresh or used dialysis fluid to exit that balance chamber on the other side of the flexible membrane. The balance chambers accordingly provide an additional layer of accuracy in case the piston pump becomes inaccurate for some reason.

The third primary embodiment includes plural fluid valves for sequencing the balance chambers and for directing a desired fresh or used PD fluid from a desired source to a desired destination. The balance chambers in an embodiment are alternated such that fresh or used PD fluid flows to or from the patient during treatment respectively. The fluid pump causes the RO water to sequence the balance chambers to move heated PD fluid around the PD fluid heat cleaning circuit. The same RO water may be used over multiple treatments and be replaced at regular service intervals.

A fourth primary embodiment is similar to the second and third primary embodiments in that it provides dedicated connectors for the reusable PD fluid lines and recirculation caps for the patient and drain line connectors. The fourth primary embodiment is also like the first primary embodiment in that a less accurate gear pump, centrifugal or other type of pump may be used, here, two gear or other pumps. The fourth primary embodiment also provides volumetric chambers having flexible membranes similar to the balancing chambers of the third primary embodiment. But here, fresh or used PD fluid is delivered and removed from one side of the volumetric chamber membranes, while air is moved back and forth on the other sides of the membranes, as opposed to the dual fluids of the third primary embodiment. In one embodiment, one of the gear, centrifugal or other type of pumps is dedicated to delivering fresh or used PD fluid to the volumetric chambers (from PD fluid containers or the patient, respectively), while the second gear or other pump is dedicated to removing fresh or used PD fluid from the volumetric chambers (to the patient or drain, respectively).

In an embodiment, a plurality of three-way valves are provided to control PD fluid flow in the fourth embodiment. A first three-way valve is provided upstream of the gear pump and is dedicated to delivering fresh or used PD fluid to the volumetric chambers. The first three-way valve determines whether fresh or used PD fluid is delivered. A second three-way valve is provided downstream of the gear pump and is dedicated to delivering fresh or used PD fluid to the volumetric chambers. The second three-way valve determines whether PD fluid is delivered to a first or a second one of the volumetric chambers. A third three-way valve is provided upstream of the gear pump and is dedicated to removing fresh or used PD fluid from the volumetric chambers. The third three-way valve determines whether PD fluid is removed from a first or a second volumetric chamber. A fourth three-way valve is provided downstream of the gear pump and is dedicated to removing fresh or used PD fluid from the volumetric chambers. The fourth three-way valve determines whether fresh PD fluid is delivered to the patient or used PD fluid is delivered to drain. A fifth three-way valve is provided to cycle back and forth between the first and second volumetric chambers during heat cleaning for example.

In an embodiment, one or more pressure sensor is provided for sensing the air pressure on the "dry" side of each of the membranes of the first and/or second volumetric chambers, which reflects PD fluid pressure on the other sides of the membranes. Where a pressure sensor is provided for each volumetric chamber, the control unit may compare the readings from the two sensors, e.g., at the startup of treatment, to confirm that the pressure sensors are measuring the same pressures. If not, the control unit may determine that one of the pressure sensors has drifted and cause a service notice to be posted on a user interface of the APD cycler. An additional pressure sensor is added in one embodiment along the patient line to provide feedback to ensure that positive and negative patient pumping pressures are within safe limits.

A fifth embodiment begins with the structure of the fourth embodiment and adds a flow sensor for tracking the volume of fresh and used PD fluid delivered to and removed from the patient. It is a goal of the fourth primary embodiment to rely on the accuracy of the volumetric chambers on a per stroke basis and to count the number of strokes to determine an overall volume of fresh and used PD fluid delivered. However, if the per stroke accuracy of the volumetric chambers is found to be not accurate enough, then the additional flow sensor may be used, wherein its output is integrated over time to determine overall fresh and used PD volumes. In one implementation, the flow sensor is placed in a location so that it may sense the flow of both fresh and used PD fluid.

A sixth embodiment begins with the structure of the fifth embodiment, including the flow sensor, which is provided again for tracking the volume of fresh and used PD fluid delivered to and removed from the patient. The sixth embodiment adds one or more valves and fluid lines so that PD fluid flows through the sensor in the same direction regardless of whether the PD fluid is fresh or used. The sixth embodiment expands the number of different flow sensors that may be used because not all flow sensors are bidirectional.

A seventh embodiment may have the same general flow paths of prior embodiments, but wherein the driving force of the membrane fluid pumps and valves is air. The benefit here is that the membrane fluid pumps are reusable and may be calibrated to high accuracy in production. Also, the fluid pump chambers can be relatively large, such that the actuation of associated membrane valves may be less frequent, which in turn should improve reliability.

In light of the disclosure set forth herein, and without limiting the disclosure in any way, in a first aspect, which may be combined with any other aspect described herein, or portion thereof, a peritoneal dialysis ("PD") system includes a housing; a dialysis fluid pump housed by the housing and including a reusable pump body that accepts PD fluid for pumping; a dialysis fluid inline heater housed by the housing and including a reusable heater body that accepts PD fluid for heating; a patient line connector presented by the housing; a drain line connector presented by the housing; a first reusable PD fluid line extending from the housing and including a first connector configured to mate with the patient line connector; a second reusable PD fluid line extending from the housing and including a second connector configured to mate with the drain line connector; and a control unit configured to run a heat cleaning sequence after a PD treatment, wherein the first connector of the first reusable PD fluid line is mated with the patient line connector, the second connector of the second reusable PD fluid line is mated with the drain line connector, and wherein the dialysis fluid pump and optionally the dialysis fluid inline heater is actuated during the heat cleaning sequence.

In a second aspect, which may be combined with any other aspect described herein, or portion thereof, the PD system includes an additional connector presented by the housing and a third reusable PD fluid line extending from the housing and including a third connector configured to mate with the additional connector for heat cleaning.

In a third aspect, which may be combined with any other aspect described herein, or portion thereof, the PD system includes a fourth fluid line including a fourth connector configured to mate with the additional connector during treatment.

In a fourth aspect, which may be combined with any other aspect described herein, or portion thereof, the fourth fluid line is used to provide additional PD fluid for treatment or a location to store an effluent sample.

In a fifth aspect, which may be combined with any other aspect described herein, or portion thereof, the PD system includes first and second PD fluid containers configured to connect to the first and second connectors, respectively.

In a sixth aspect, which may be combined with any other aspect described herein, or portion thereof, the first and second connectors are different from each other.

In a seventh aspect, which may be combined with any other aspect described herein, or portion thereof, the PD includes a disposable patient line configured to connect to the patient line connector and a disposable drain line configured to connect to the drain line connector.

In an eighth aspect, which may be combined with any other aspect described herein, or portion thereof, at least one of the first or second reusable PD fluid lines is provided with a one or more lid that is opened and closed to disconnect and connect, respectively, the first connector from and to the patient line connector or the second connector from and to the drain line connector.

In a ninth aspect, which may be combined with any other aspect described herein, or portion thereof, the control unit is configured to cause (i) the dialysis fluid inline heater to heat the PD fluid to at least 70° C. or at least 120° C. for a sterilization level of heat cleaning and (ii) the dialysis fluid pump to recirculate the heated PD fluid during the heat cleaning sequence.

In a tenth aspect, which may be combined with any other aspect described herein, or portion thereof, the dialysis fluid pump is a piston, gear or membrane pump, the reusable pump body of the piston, gear or membrane pump accepting PD fluid for pumping.

In an eleventh aspect, which may be combined with any other aspect described herein, or portion thereof, a peritoneal dialysis ("PD") system includes a housing; a dialysis fluid pump housed by the housing and including a reusable pump body that accepts PD fluid for pumping; a dialysis fluid inline heater housed by the housing and including a reusable heater body that accepts PD fluid for heating; a patient line connector presented by the housing, the patient line connector including a patient line recirculation cap enabling PD fluid to be recirculated through the patient line connector when sealingly capped by the patient line recirculation cap; a drain line connector presented by the housing, the drain line connector including a drain line recirculation cap enabling PD fluid to be recirculated through the drain line connector when sealingly capped by the drain line recirculation cap; at least one reusable PD fluid line; at least one heat cleaning connector supported by the housing and configured to accept one of the at least one reusable PD fluid line; and a control unit configured to run a heat cleaning sequence after a PD treatment, wherein the patient line connector is capped by the patient line recirculation cap, wherein the drain line connector is capped by the drain line recirculation cap, wherein each of the at least one reusable PD fluid line is connected to one of the at least one heat cleaning connectors, and wherein at least one of the dialysis fluid pump or the dialysis fluid inline heater is actuated during the heat cleaning sequence.

In a twelfth aspect, which may be combined with any other aspect described herein, or portion thereof, the control unit is configured to perform a first PD fluid flow determination using first and second dialysis fluid temperature measurements of the PD fluid heated by a heater under control of the control unit, and to compare the first PD fluid flow determination to a second PD fluid flow determination that is based on a corresponding actuation of the dialysis fluid pump.

In a thirteenth aspect, which may be combined with any other aspect described herein, or portion thereof, the PD system includes at least one cover positioned and arranged to releasably and sealingly cap the at least one heat cleaning connector during the heat cleaning sequence.

In a fourteenth aspect, which may be combined with any other aspect described herein, or portion thereof, at least one of the patient line recirculation cap or the drain line recirculation cap includes an internal passageway for recirculation.

In a fifteenth aspect, which may be combined with any other aspect described herein, or portion thereof, the PD system includes at least one PD fluid container configured to accept one of the at least one reusable PD fluid line.

In a sixteenth aspect, which may be combined with any other aspect described herein, or portion thereof, the PD system includes a disposable patient line configured to connect to the patient line connector and a disposable drain line configured to connect to the drain line connector.

In a seventeenth aspect, which may be combined with any other aspect described herein, or portion thereof, the control unit is configured to cause (i) the dialysis fluid inline heater to heat the PD fluid to at least 70° C. or at least 120° C. for a sterilization level of heat cleaning and (ii) the dialysis fluid pump to recirculate the heated PD fluid during the heat cleaning sequence.

In an eighteenth aspect, which may be combined with any other aspect described herein, or portion thereof, the dialysis fluid pump is a piston, gear or membrane pump, the reusable pump body of the piston, gear or membrane pump accepting PD fluid for pumping.

In a nineteenth aspect, which may be combined with any other aspect described herein, or portion thereof, a peritoneal dialysis ("PD") system includes a housing; a patient line connector presented by the housing, the patient line connector including a patient line recirculation cap enabling PD fluid to be recirculated through the patient line connector when sealingly capped by the patient line recirculation cap; a drain line connector presented by the housing, the drain line connector including a drain line recirculation cap enabling PD fluid to be recirculated through the drain line connector when sealingly capped by the drain line recirculation cap; at least one reusable PD fluid line; at least one heat cleaning connector supported by the housing and configured to accept the at least one reusable PD fluid line; at least one fixed volume chamber including a flexible membrane separating a process fluid side of the chamber from a PD fluid side of the chamber; a process fluid pump configured to pump process fluid to and from the process fluid side of the at least one fixed volume chamber to respectively discharge PD fluid from and draw PD fluid into the PD fluid side of the at least one fixed volume chamber; a dialysis fluid inline heater housed by the housing and in fluid communication with the PD fluid side of the at least one fixed volume chamber; and a control unit configured to run a heat cleaning sequence after a PD treatment, wherein the patient line connector is capped by the patient line recirculation cap, wherein the drain line connector is capped by the drain line recirculation cap, wherein each of the at least one reusable PD fluid line is connected to one of the at least one heat cleaning connectors, and wherein the process fluid pump and optionally the dialysis fluid inline heater are actuated during the heat cleaning sequence.

In a twentieth aspect, which may be combined with any other aspect described herein, or portion thereof, the dialysis fluid inline heater is in selective fluid communication with the PD fluid side of the at least one fixed volume chamber via at least one valve.

In a twenty-first aspect, which may be combined with any other aspect described herein, or portion thereof, the at least one fixed volume chamber includes first and second fixed volume chambers, each chamber including a flexible membrane separating a process fluid side of the first or second chamber from a PD fluid side of the first or second chamber, and wherein the process fluid pump is positioned and arranged to pump process fluid to the process fluid side of one of the first or second chambers while pumping process fluid from the other of the first or second chambers.

In a twenty-second aspect, which may be combined with any other aspect described herein, or portion thereof, the process fluid is water or air.

In a twenty-third aspect, which may be combined with any other aspect described herein, or portion thereof, the process fluid pump is a piston pump, and wherein the process fluid is used additionally as a flush fluid for the piston pump.

In a twenty-fourth aspect, which may be combined with any other aspect described herein, or portion thereof, the process fluid pump is in fluid communication with the process fluid side of the at least one fixed volume chamber via a process fluid circuit, and wherein the process fluid circuit includes a storage chamber for storing an additional amount of process fluid.

In a twenty-fifth aspect, which may be combined with any other aspect described herein, or portion thereof, the dialysis fluid inline heater is located between the at least one least one reusable PD fluid line and the PD fluid side of the at least one fixed volume chamber.

In a twenty-sixth aspect, which may be combined with any other aspect described herein, or portion thereof, the PD system includes a first valve between each of the at least one reusable PD fluid line and the dialysis fluid inline heater and at least one second valve between the dialysis fluid inline heater and the PD fluid side of each of the at least one fixed volume chamber.

In a twenty-seventh aspect, which may be combined with any other aspect described herein, or portion thereof, the patient line connector when sealingly capped by the patient line recirculation cap is in fluid communication with (i) a fresh or used PD fluid line extending from the PD fluid side of each of the at least one fixed volume chamber and (ii) a heat cleaning line extending to each of the at least one heat cleaning connector.

In a twenty-eighth aspect, which may be combined with any other aspect described herein, or portion thereof, the patient line connector when uncapped by the patient line recirculation cap is in fluid communication with (i) the fresh or used PD fluid line extending from the PD fluid side of each of the at least one fixed volume chamber and (ii) a disposable patient line.

In a twenty-ninth aspect, which may be combined with any other aspect described herein, or portion thereof, the drain line connector when sealingly capped by the drain line recirculation cap is in fluid communication with (i) a used PD fluid line extending from the PD fluid side of each of the at least one fixed volume chamber and (ii) the heat cleaning line extending to each of the at least one heat cleaning connector.

In a thirtieth aspect, which may be combined with any other aspect described herein, or portion thereof, the drain line connector when uncapped by the patient line recirculation cap is in fluid communication with (i) the used PD fluid line extending from the PD fluid side of each of the at least one fixed volume chamber and a disposable drain line.

In a thirty-first aspect, which may be combined with any other aspect described herein, or portion thereof, a peritoneal dialysis ("PD") system includes a housing; a patient line connector presented by the housing, the patient line connector including a patient line recirculation cap enabling PD fluid to be recirculated through the patient line connector when sealingly capped by the patient line recirculation cap; a drain line connector presented by the housing, the drain line connector including a drain line recirculation cap enabling PD fluid to be recirculated through the drain line connector when sealingly capped by the drain line recirculation cap; at least one reusable PD fluid line; at least one heat cleaning connector supported by the housing and configured to accept the at least one reusable PD fluid line; at least one fixed volume chamber including a flexible membrane separating a compressible fluid side of the chamber from a PD fluid side of the chamber; at least one PD fluid pump configured to pump PD fluid to and from the PD fluid side of the at least one fixed volume chamber to respectively pressurize the compressible fluid and depressurize the compressible fluid; a dialysis fluid inline heater housed by the housing and in fluid communication with the PD fluid side of the at least one fixed volume chamber; and a control unit configured to run a heat cleaning sequence after a PD treatment, wherein the patient line connector is capped by the patient line recirculation cap, wherein the drain line connector is capped by the drain line recirculation cap, wherein each of the at least one reusable PD fluid line is connected to one of the at least one heat cleaning connectors, and wherein the PD fluid pump and optionally the dialysis fluid inline heater is actuated during the heat cleaning sequence.

In a thirty-second aspect, which may be combined with any other aspect described herein, or portion thereof, the dialysis fluid inline heater is in selective fluid communication with the PD fluid side of the at least one fixed volume chamber via at least one valve.

In a thirty-third aspect, which may be combined with any other aspect described herein, or portion thereof, the at least one fixed volume chamber includes first and second fixed volume chambers, each chamber including a flexible membrane separating a compressible fluid side of the first or second chamber from a PD fluid side of the first or second chamber, and wherein the at least one PD fluid pump is positioned and arranged to pump PD fluid to the PD fluid side of one of the first or second chambers while pumping PD fluid from the other of the first or second chambers.

In a thirty-fourth aspect, which may be combined with any other aspect described herein, or portion thereof, the PD system includes a compressible fluid circuit extending between the compressible fluid sides of the first and second fixed volume chambers, the compressible fluid circuit enabling (i) compressible fluid pushed from one of the compressible fluid sides to enter the other of the compressible fluid sides or (ii) compressible fluid to be vented to atmosphere.

In a thirty-fifth aspect, which may be combined with any other aspect described herein, or portion thereof, wherein the compressible fluid is air.

In a thirty-sixth aspect, which may be combined with any other aspect described herein, or portion thereof, the at least one PD fluid pump includes first and second PD fluid pumps, which are each positioned and arranged to pump fresh and used PD fluid to and from the at least one fixed volume chamber.

In a thirty-seventh aspect, which may be combined with any other aspect described herein, or portion thereof, the PD system includes at least one three-way valve selected from (i) a first three-way valve positioned and arranged to direct fresh or used PD fluid to a first or a second fixed volume chamber, (ii) a second three-way valve positioned and arranged to direct fresh or used PD fluid to the first or second fixed volume chamber, (iii) a third three-way valve positioned and arranged to direct fresh PD fluid from and used PD fluid to the first or second fixed volume chamber, (iv) a forth three-way valve positioned and arranged to direct fresh PD fluid to or used PD fluid from the patient line connector and to direct used PD fluid, or air, or fresh PD fluid to the drain line connector, or (v) a fifth three-way valve positioned and arranged to toggle back and forth between the first or second fixed volume chambers during the heat cleaning sequence.

In a thirty-eighth aspect, which may be combined with any other aspect described herein, or portion thereof, the dialysis fluid inline heater is located between the at least one least one reusable PD fluid line and the PD fluid side of the at least one fixed volume chamber.

In a thirty-ninth aspect, which may be combined with any other aspect described herein, or portion thereof, the patient line connector when sealingly capped by the patient line recirculation cap is in fluid communication with (i) a fresh or used PD fluid line and (ii) a heat cleaning line extending to each of the at least one heat cleaning connector.

In a fortieth aspect, which may be combined with any other aspect described herein, or portion thereof, the patient line connector when uncapped by the patient line recirculation cap is in fluid communication with (i) the fresh or used PD fluid line and (ii) a disposable patient line.

In a forty-first aspect, which may be combined with any other aspect described herein, or portion thereof, the drain line connector when sealingly capped by the drain line recirculation cap is in fluid communication with (i) a used PD fluid line and (ii) the heat cleaning line extending to each of the at least one heat cleaning connector.

In a forty-second aspect, which may be combined with any other aspect described herein, or portion thereof, the drain line connector when uncapped by the patient line recirculation cap is in fluid communication with (i) the used PF fluid line and (ii) a disposable drain line.

In a forty-third aspect, which may be combined with any other aspect described herein, or portion thereof, the PD system includes a flowmeter outputting to the control unit, the at least one flowmeter positioned and arranged to measure the flowrate of fresh and used PD fluid.

In a forty-forth aspect, which may be combined with any other aspect described herein, or portion thereof, the PD system is configured such that fresh and used PD fluid travel a same direction through the flowmeter.

In a forty-fifth aspect, any of the features, functionality and alternatives described in connection with any one or more of FIGS. 1 to 6 may be combined with any of the features, functionality and alternatives described in connection with any other of FIGS. 1 to 6.

It is accordingly an advantage of the present disclosure to provide an automated peritoneal dialysis ("APD") cycler that reuses many components, which may otherwise be disposable.

It is another advantage of the present disclosure to provide an APD cycler having fluid handling components that accept peritoneal dialysis fluid directly without having to operate with a disposable item, such as a tube or flexible sheeting.

It is a further advantage of the present disclosure to provide an APD cycler that may use unused, remaining PD fluid during heat cleaning.

It is yet another advantage of the present disclosure to provide a volumetrically accurate automated peritoneal dialysis APD cycler.

It is yet a further advantage of the present disclosure to provide an APD cycler having fluid pressure control pumping to and from the patient.

It is still another advantage of the present disclosure to provide a relatively quiet APD cycler.

It is still a further advantage of the present disclosure to provide a relatively simple disposable set.

Yet another advantage of the present disclosure is to provide a reusable fluid circuit having a small total volume such that the PD fluid remaining in the PD fluid containers at the end of treatment is enough to fill and heat clean the entire volume of the reusable fluid circuit.

Still another advantage of the present disclosure is to provide an APD system in which a patient line from a first APD treatment is used as a drain line in a second APD treatment.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

DETAILED DESCRIPTION

Figure 1:
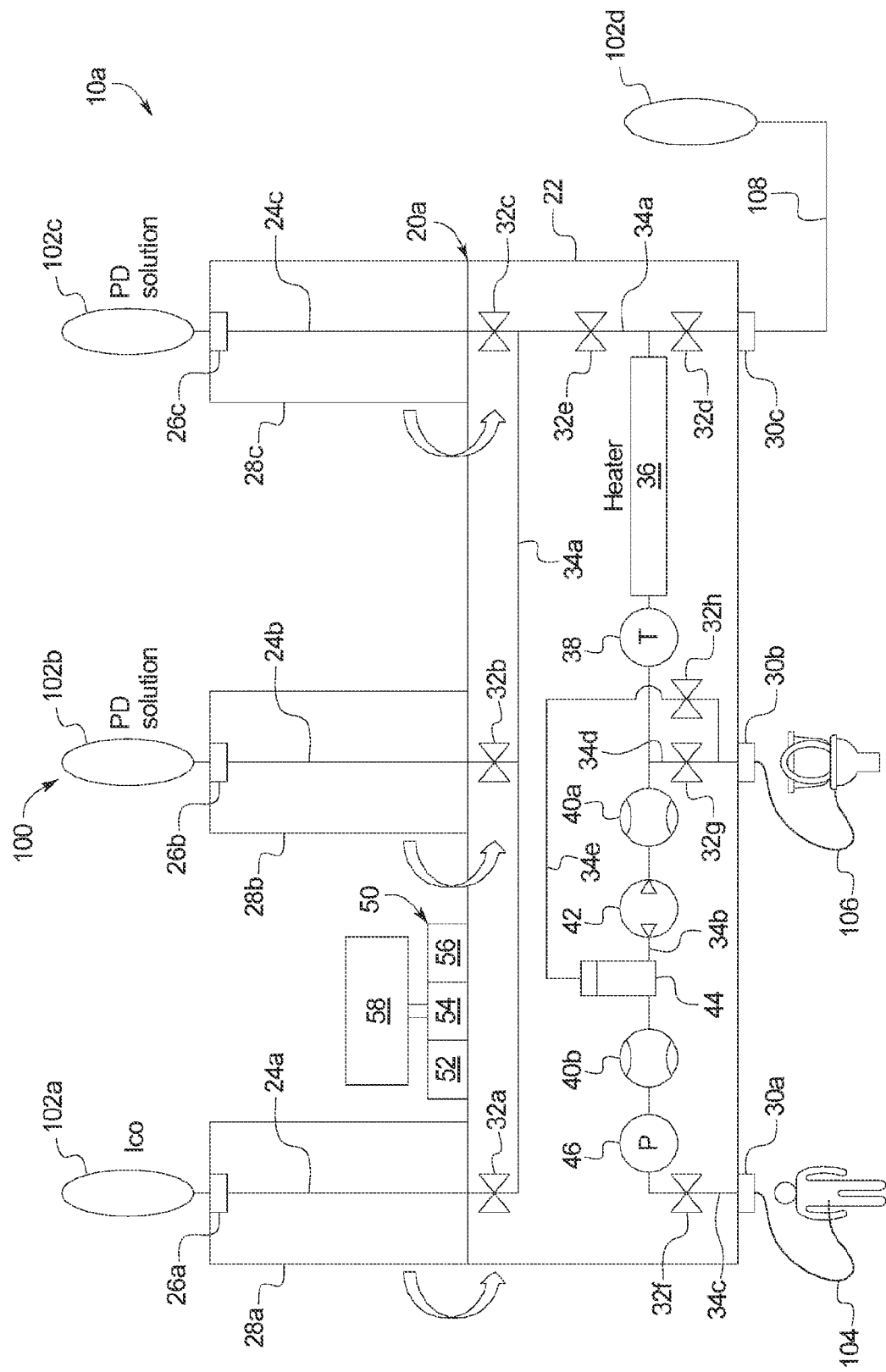
FIG. 1 is a schematic view of one embodiment of an automated peritoneal dialysis ("APD") cycler and associated system using heat cleaning of the present disclosure.

Referring now to the drawings and in particular to FIG. 1, an automated peritoneal dialysis ("APD") system 10*a* and associated methodology of the present disclosure includes an APD machine or cycler 20*a*. System 10*a* and cycler 20*a* (as do other systems and cyclers described herein) attempt to eliminate disposable items as much as possible and instead provide a majority of its fluid carrying portions as reusable components, which are disinfected or sterilized along with the flowpath of cycler 20*a* between treatments. Fluid lines within the machine or cycler are reused. In particular, FIG. 1 illustrates that cycler 20*a* includes a housing 22 from which reusable PD fluid lines 24*a* to 24*c* extend. Reusable PD fluid lines 24*a* to 24*c* extend respectively to reusable line connectors 26*a* to 26*c*. Reusable PD fluid lines 24*a* to 24*c* and line connectors 26*a* to 26*c* in the illustrated embodiment are provided respectively in lids 28*a* to 28*c*, which may for example be attached via hinges to housing 22. Lids 28*a* to 28*c* hinge open to enable line connectors 26*a* to 26*c* to connect to disposable PD fluid containers 102*a* to 102*c*. Lids 28*a* to 28*c* hinge closed to enable line connectors 26*a* to 26*c* to connect instead to reusable cycler connectors 30*a* to 30*c*, respectively.

As used herein, "heat cleaning" may mean "heating over time to at least a sufficient disinfection level and perhaps to a sterilization level". The practical difference between a disinfection level and sterilization level is that if the cycler flowpaths and components are sterilized or cleaned to a sterilization level then no further filtration is needed. If the cycler flowpaths and components are disinfected or cleaned to a disinfection level then some sort of filtration, e.g., one or more sterile, sterilizing grade filter in patient line 104 (not illustrated and which may itself be sterilized), is provided. It is a goal of each of systems 10*a* to 10*f* described herein to heat clean the cycler flowpaths and components to a sterilization level such that an additional filter is not needed. However, if it is found that a sterilization level cannot be met or met consistently, then additional filtration, e.g., sterilizing grade filter in patient line 104 (not illustrated), needs to be provided. Accordingly, "heat cleaned" as used herein may mean at least disinfected and sterilized if possible.

PD fluid containers 102*a* to 102*c* may be provided as part of a disposable set 100, e.g., sterilized, along with a disposable patient line 104, a disposable drain line 106 and a possible extra disposable supply line 108. In an alternative embodiment, disposable set 100. e.g., sterilized, includes disposable patient line 104, disposable drain line 106 and possibly extra disposable supply line 108, but wherein PD fluid containers 102*a* to 102*c* are provided separately to be connected to reusable PD fluid lines 24*a* to 24*c* at the start of treatment. Disposable patient line 104 extends to a patient for treatment, while disposable drain line 106 may extend to a disposable drain container or to a house drain. Disposable set 100 may further include an optional fourth PD fluid container 102*d*, which connects during treatment to reusable cycler connector 30*c* via a disposable supply line 108. Any of reusable PD fluid lines 24*a* to 24*c*, any of the reusable tubing located within cycler 20*a*, any portion of housing 22, and any portion of disposable set 100 may be made of metal, e.g., stainless steel, steel or plastic, e.g., polyether ether ketone ("PEEK"), polyvinylchloride ("PVC") or a non-PVC material, such as polyethylene ("PE"), polyurethane ("PU") or polycarbonate ("PC").

In one embodiment, the disposable patient line 104 in a first treatment is used as a disposable drain line 106 in a second treatment. Reusing disposable patient line 104 as a future drain line further conserves disposable waste and is contemplated for each of systems 10*a* to 10*f* discussed herein.

Multiple embodiments are contemplated to prevent the used patient line from being used again as a new patient line. One way to do so is mechanically. For example, with patient cycler connector 30*a* being different than drain cycler connector 30*b*, disposable patient line 104 is configured such that after treatment the end previously connected to patient cycler connector 30*a* is connected instead to the other end of disposable patient line 104, which had been connected to the patient's transfer set, forming a loop for storage between treatments, and wherein the connection forming the loop is permanent so that the end previously connected to patient cycler connector 30*a* cannot be reconnected to the patient cycler connector. The connector for connecting to drain cycler connector 30*b* is provided elsewhere in the loop covered by a frangible cover that is removed for the second treatment to expose the disposable drain connector, which for example unthreads from a mating connector to undue the loop.

In another mechanical example, again with patient cycler connector 30*a* being different than drain cycler connector 30*b*, disposable patient line 104 is configured such that the disposable patient connector connected previously to patient cycler connector 30*a* is connected at its other end to the disposable drain connector or a short line leading to the disposable drain connector. Here, the disposable drain connector has to be exposed first before use.

Another or additional way to help prevent reuse of disposable patient line 104 as a patient line in a second treatment is to chemically alter the patient line. In one example, the reusable patient cycler connector 30*a* and reusable drain cycler connector 30*b* have the same configuration so that drain cycler connector 30*b* receives the same end of disposable patient line 104 used previously as the patient line. It is contemplated to provide that end of patient line 104 with a patient/drain line connector having an indicator that changes color, for example, when contacted by PD fluid, so that the patient or caregiver attaching patient line 104 and drain line 106 for a new treatment can readily discern which line to attach to drain cycler connector 30*b*.

PD fluid containers 102*a* to 102*d* may hold different dextrose or glucose level dialysis fluids, such as 1.36% glucose dialysis fluid, 2.27% glucose dialysis fluid and/or a last bag of a different formulation of PD fluid, such as icodextrin. In the illustrated embodiment, PD fluid containers 102*b* to 102*d* hold a 1.36% glucose or 2.27% glucose dialysis fluid, e.g., one or more fill volume's worth of PD fluid, while PD fluid container 102*a* holds a single last fill volume of icodextrin, which is formulated to remain within the patient for an extended period of time.

In the illustrated embodiment, all components located within cycler 20*a* are reusable, reducing the disposable materials to those listed above for disposable set 100. PD fluid valves 32*a* to 32*e* allow a selected PD fluid to flow along a reusable inlet line 34*a* to a reusable heater 36. In an embodiment, each of the valves of APD cycler 20*a*, including PD fluid valves 32*a* to 32*e*, is an electrically actuated valve having a reusable valve body that closes (e.g., when unpowered for fail safe operation) or opens to allow (e.g., when powered) PD fluid to flow through the body. Bi-stable valves may be used alternatively, perhaps only in non-critical safety locations. Dialysis fluid inline heater 36 is also electrically actuated in one embodiment and is, for example, a resistive heater having a reusable heater body that accepts PD fluid for treatment and heat cleaning (e.g., heat disinfection or heat sterilization).

Inline heater 36 in an embodiment is able to heat PD fluid from room temperature or colder (e.g., if the PD fluid is stored in a cold environment) to body temperature, e.g., 37° C., at a flowrate of at least 300 milliliters ("ml")/minute. Lower flowrates may also be achieved, e.g., for children or infants. A temperature sensor 38 is located adjacent to heater 36, e.g., downstream from the heater to provide feedback for temperature control. If desired, a second temperature sensor (not illustrated) may be provided upstream from heater 36 to enable the incoming temperature of fresh PD fluid to be taken into account in the heating algorithm. Heater 36 and temperature sensor 38 may serve as a flow meter as discussed in more detail herein, e.g., as either a control or protective/safety flowmeter.

A reusable pumping line 34*b* extends downstream from inline heater 36. A number of fluid components are located along reusable pumping line 34*b*, including a first flowmeter 40*a*, a second flowmeter 40*b* and a PD fluid pump 42 located between first and second flowmeters 40*a* and 40*b*. Flowmeters 40*a* and 40*b* in an embodiment are electromagnetic or Coriolis type flowmeters. Flowmeters 40*a* and 40*b* are reusable and may be used not only to regulate flowrate but also to integrate fresh and used PD fluid volume over the course of a treatment so that it is known at the end of treatment how much fresh PD fluid has been delivered to the patient and how much used PD fluid has been removed from the patient. The difference between the two equals the total amount of fluid removed from the patient over treatment, at least some of which may be ultrafiltration ("UF") removed, which is an important parameter to achieve and monitor.

In one implementation of a patient fill in FIG. 1 (fresh PD fluid flowing from right to left), flowmeter 40*b* is used as the primary control flowmeter because it is more accurate due to air bubbles having been removed in air trap 44 upstream from flowmeter 40*b* (flowmeter 40*a* is used as protective or safety flowmeter). During a patient drain in which the flow direction is reversed (used PD fluid flowing from left to right), flowmeter 40*a* is used as the primary control flowmeter because it is now more accurate due to air bubbles having been removed in air trap 44 upstream from flowmeter 40*a* (flowmeter 40*b* is used as protective or safety flowmeter).

The provision of flowmeters 40*a* and 40*b* enables a less accurate PD fluid pump 42, such as a gear pump, centrifugal or other type of pump, to be used. PD fluid pump 42 includes a reusable pump body that accepts PD fluid for pumping. That is, PD pump 42 does not require the PD fluid to flow within a disposable item, such as a tube or cassette. The reusable pump body of pump 42 itself accepts the PD fluid. Dialysis fluid pump 42 is controllable to pump to and from the patient at or below a pressure limit by controlling a level of current, voltage, or voltage pulse train to the PD fluid pump. A positive patient pressure limit may for example be one to five psig (e.g., two psig (14 kPa). A negative patient pressure limit may for example be −1.0 psig to −3.0 psig (e.g., −1.3 psig (−9 kPa)). Pump 42 is also capable of supplying lower pressures if needed, e.g., for small children or babies. Dialysis fluid pump 42 is bidirectional and continuous in one embodiment, such that a single pump may be provided.

Two bidirectional flowmeters 40a and 40b may be provided so that their outputs may be compared to ensure accuracy. Also, certain flowmeters are single direction, wherein one of flowmeter 40b is used for patient filling, while the other flowmeter is used for patient draining. Also, if a certain flowmeter works better under positive or negative pressure, then flowmeters 40a and 40b may be arranged accordingly on the appropriate side of PD fluid pump 42. If two single direction flowmeters 40a and 40b are provided, then two additional single direction flowmeters or perhaps a single bidirectional flowmeter may be provided, wherein single direction flowmeters 40a and 40b are used for control and the other one or more flowmeter is used for redundancy/protection in case of a hazardous situation due to a malfunctioning component.

In the illustrated embodiment, an air trap 44 is located between PD fluid pump 42 and flowmeter 40a and 40b, however, air trap 44 may be located in alternative positions along reusable pumping line 34b. In one preferred embodiment, air trap 44 is located somewhere between flowmeters 40a and 40b. Air trap 44 removes air from fresh PD fluid prior to reaching the patient. The extra volume may for example be useful during heat cleaning (e.g., heat disinfection or heat sterilization). Air trap 44 may be provided with any of cyclers 20a to 20f of the respective systems described herein even if not illustrated.

A pressure sensor 46 is located along reusable patient line 34c between flowmeter 40b and the patient. Pressure sensor 46 records the pressure of fresh PD fluid delivered to the patient and used PD fluid removed from the patient. The pressure readings are used to control PD fluid pump 42 so that the pressure of fresh and used PD fluid flow remains within the patient pressure limits listed above.

Reusable patient line 34c extends from flowmeter 40b to reusable patient cycler connector 30a. A reusable drain line 34d extends from patient line 34b to reusable drain cycler connector 30b. A reusable vent line 34e extends from the top of air trap 44 to drain line 34d to enable air to be delivered to drain. A patient valve 32f is located along reusable patient line 34c. A drain valve 32g is located along reusable drain line 34d. A vent valve 32h is located along reusable vent line 34e. Valves 32f to 32h may likewise be electrically actuated valves having a reusable valve body that closes (e.g., when unpowered for fail safe operation) or opens to allow (e.g., when powered) fresh or used PD fluid or air to flow through the body.

FIG. 1 illustrates that APD cycler 20a of system 10a of the present disclosure includes a control unit 50 having one or more processor 52 and one or more memory 54 that receive, store and process signals or outputs from flowmeters 40a, 40b, pressure sensor(s) 46, temperature sensor(s) 38, an optional conductivity sensor (shown below) and perhaps lid position sensors to detect if connectors 26a to 26c of lids 28a to 28c, respectively, are attached or not (to enable treatment to start or to alarm respectively). Control unit 50 uses pressure feedback to control dialysis fluid pump 42 to pump fresh and used PD fluid at safe patient and system pressure limits. Control unit 50 uses temperature feedback to control inline dialysis fluid heater 36 to heat the fresh dialysis fluid to, e.g., body temperature, and to heat the cleaning fluid at the end of treatment to clean (disinfect or sterilize) the reusable fluid pathways of cycler 20a. Control unit 50 uses temperature compensated conductivity readings to analyze fresh and/or used dialysis fluid for reasons discussed herein.

Control unit 50 also includes a video controller 56 that interfaces with a user interface 58, which may include a display screen operating with a touchscreen and/or one or more electromechanical button, such as a membrane switch. User interface 58 may also include one or more speaker for outputting alarms, alerts and/or voice guidance commands. User interface 58 may be provided with cycler 20a as illustrated in FIG. 1 and/or be a remote user interface operating with control unit 50. Control unit 50 may also include a transceiver (not illustrated) and a wired or wireless connection to a network, e.g., the internet, for sending treatment data to and receiving prescription instructions from a doctor's or clinician's server interfacing with a doctor's or clinician's computer.

Control unit 50 also opens and closes dialysis fluid valves 32a to 32h in different combinations with the operation of dialysis fluid pump 42 and heater 36 to run a priming sequence, multiple patient fill sequences, multiple patient drain sequences, and a heat cleaning (e.g., heat disinfection or heat sterilization) sequence at the end of a PD treatment.

Cycler 20a as illustrated in FIG. 1 is in a treatment configuration with lids 28a to 28c open to allow (i) reusable PD fluid line 24a to be connected to disposable PD fluid container 102a, (ii) reusable PD fluid line 24b to be connected to disposable PD fluid container 102b, (iii) reusable PD fluid line 24c to be connected to disposable PD fluid container 102c, (iv) reusable patient cycler connector 30a to be connected to disposable patient line 104, and (v) reusable drain cycler connector 30b to be connected to disposable drain line 106. Containers 102a to 102c may be disposable and include ports or small disposable lines for connecting to reusable lines 24a to 24c, respectively. In the illustrated embodiment, optional disposable PD fluid container 102d is connected via disposable supply line 108 to reusable supply connector 30c. If optional disposable PD fluid container 102d and disposable supply line 108 are not provided, reusable supply connector 30c may either be configured to spring-closed itself or to be closed via a separate (possibly tethered) cap.

At the end of a treatment and perhaps after each of PD fluid containers 102a to 102d have been emptied, the disposable items are removed: (i) disposable PD fluid container 102a is removed from reusable line connector 26a, (ii) disposable PD fluid container 102b is removed from reusable line connector 26b, (iii) disposable PD fluid container 102c is removed from reusable line connector 26c, (iv) patient line 104 is removed from reusable patient cycler connector 30a, (v) disposable drain line 106 is removed from reusable drain cycler connector 30b, and (v) disposable supply line 108 if provided is removed from reusable cycler connector 30c. For heat cleaning (e.g., heat disinfection or heat sterilization), the user (i) closes lid 28a so that reusable line connector 26a connects to reusable patient cycler connector 30a, (ii) closes lid 28b so that reusable line connector 26b connects to reusable drain cycler connector 30b, and (iii) closes lid 28c so that reusable line connector 26c connects to reusable cycler connector 30c.

The provision of lids 28a to 28c makes the improper connection of reusable line connectors 26a to 26c to reusable cycler connectors 30a to 30c unlikely, nevertheless, it is contemplated here and in all other system and cycler embodiments described herein to make line connectors 26a to 26c and cycler connectors 30a to 30c color coded and/or keyed for matching pairs of connectors.

With lids 28a to 28c closed and connectors 26a/30a, 26b/30b, 26c/30c connected, the fluid circuit of cycler 20a is likewise closed for heat cleaning (e.g., heat disinfection or heat sterilization). Control unit 50 in an embodiment causes all valves 32a to 32h to open, runs PD fluid pump 42 and energizes heater to circulate heated cleaning fluid, e.g., multiple times, through the closed cleaning loop including reusable PD fluid lines 24a to 24c, reusable inlet line 34a, reusable pumping line 34b, reusable patient line 34c, reusable drain line 34d and reusable vent line 34e. The cleaning fluid is in one embodiment PD fluid, e.g., fresh PD fluid, which is heated to a disinfection or sterilization temperature, e.g., between 70° C. and 130° C., e.g., 70° C. for disinfection and 120° C. and above for sterilization. Various valves 32a to 32h may be toggled open and closed if desired and PD fluid pump 42 may reverse direction one or more times. The heat cleaning (e.g., heat disinfection or heat sterilization) sequence for system 10a lasts until a sufficient heat cleaning dose (e.g., AO dose) is provided to properly clean (disinfect or sterilize) each of the lines and all components in contact with the reusable fluid path listed above and discussed herein.

In an alternative embodiment, reusable cycler connectors 30a to 30c become line connectors and are moved respectively to the ends of patient line 104, drain line 106 and supply line 108. If optional supply container 102d is not used, reusable line connector may again be configured to spring-close itself or be capped via a separate, e.g., tethered, cap. At the end of treatment, all disposable PD fluid containers 102a to 102d are removed and line connectors 30a to 30c are connected to reusable PD fluid lines 24a to 24c to close the heat cleaning loop. Control unit 50 runs the heat cleaning (e.g., heat disinfection or heat sterilization) sequence as described above. In this alternative embodiment, lids 28a to 28c may or may not be provided.

Figure 2:
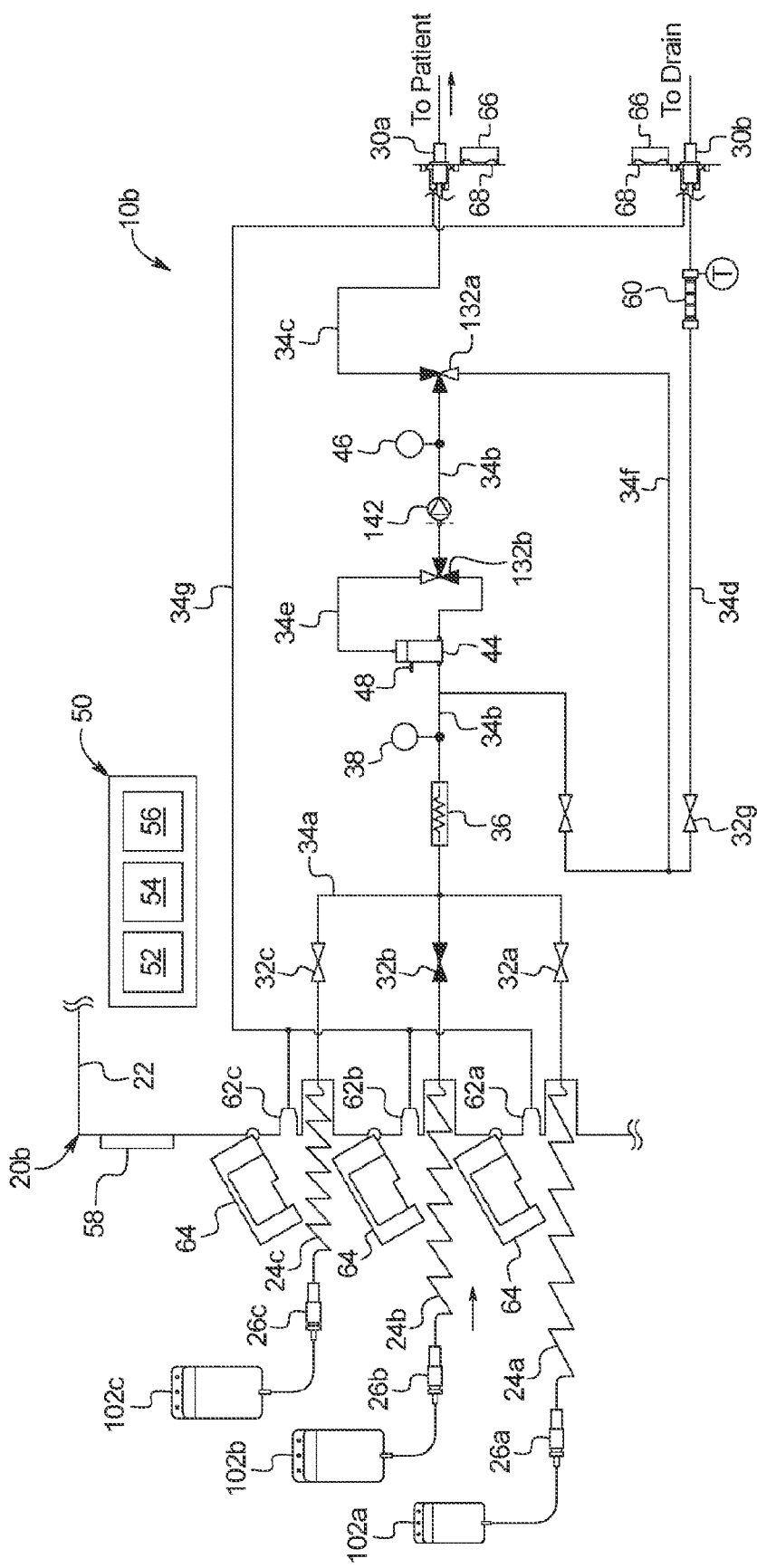
FIG. 2 is a schematic view of a second embodiment of an APD cycler and associated system using heat cleaning of the present disclosure.

Referring now to FIG. 2, an alternative APD system 10b and associated methodology of the present disclosure includes an APD machine or cycler 20b. System 10b includes many of the same components as system 10a, which are numbered the same, which may or may not be described in connection with system 10b, but which in any case include all of the structure, functionality and alternatives discussed in connection with system 10a. In particular, cycler 20b includes a housing 22 holding PD fluid valves 32a to 32c and drain valve 32g, reusable inlet line 34a, inline heater 36, at least one temperature sensor 38, air trap 44, reusable pumping line 34b, at least one pressure sensor 46, reusable patient line 34c, reusable drain line 34d, reusable vent line 34e, drain valve 32g, control unit 50 and user interface 58. Cycler 20b also includes reusable PD fluid lines 24a to 24c extending respectively to reusable line connectors 26a to 26c. Reusable patient cycler connector 30a and reusable drain cycler connector 30b are also provided.

Differences with alternative APD system 10b include the removal of flowmeters 40a and 40b and the replacement of pump 42, e.g., a less accurate gear or other pump, with a highly inherently accurate piston or membrane pump 142 under control of control unit 50, which accurately pumps total fresh PD fluid delivered, total used PD fluid removed and in doing so allows control unit 50 to accurately calculate the patient's fluid (e.g., UF) removed over the course of a treatment. Piston pump 142 may require a flush flow of a fluid, such as reverse osmosis ("RO") water during treatment for lubrication, which is supplied for example via a water pump (not illustrated) under control of control unit 50 from an RO water source. Piston pump 142 like all pumps herein includes a body that accepts fresh or used dialysis fluid and does not operate with a disposable component.

To confirm the inherent accuracy of piston pump 142, control unit 50 may at the start of each patient fill, pump first few milliliters of fresh PD fluid through heater 36 without heating the fluid. A first temperature measurement T1 is taken at temperature sensor 38. Heater 36 is then energized and the effect needed to raise the temperature to T2 as measured at temperature sensor 38, e.g., the filling temperature of 37° C., provides a measurement of PD fluid flow. The accuracy of piston pump 142 may be checked using dialysis fluid inline heater 36. Here, at the start of each patient fill, control unit 50 causes a first few milliliters of fresh PD fluid to be pumped through heater 36 without heating the fluid. Control unit 50 causes a first temperature measurement T1 to be taken. Control unit 50 then causes heater 36 to be energized and the effect needed to raise the temperature to T2, e.g., the filling temperature of 37° C., is measured and provides a measurement of PD fluid flow. Control unit 50 knows the specific heat capacity for water and the temperature delta (T2–T1), which the control unit uses to convert a heating effect (energy/time) to flowrate (mass/time). If the difference between what control unit 50 calculates fluid pump 142 to have pumped and the value determined via heater 36 is outside of a limit, then control unit 50 causes user interface 58 to inform the user that pump 142 needs to be recalibrated and/or sends a communication over a network to a service portal indicating same. The redundant volumetric calculation and associated check using heater 36 may be performed with any of systems 10a to 10f discussed herein.

Another difference with system 10b includes the provision of one or more level sensor 48 (may also be provided with system 10a) with air trap 44 and outputting to control unit 50. One or more level sensor 48 enables a particular level or range of levels of fresh PD fluid to be maintained in air trap 44. One or more level sensor 48 may be provided with any of the air traps discussed herein. System 10b includes a conductivity sensor 60 located along reusable drain line 34d, which outputs to control unit 50, and which may be temperature compensated. Conductivity sensor 60 may be used, e.g. during priming, to detect the conductivity of fresh PD fluid to make sure that it is of a prescribed type, e.g., of a prescribed glucose or dextrose level. Conductivity sensor 74 may alternatively or additionally be used. e.g., during priming, to detect the conductivity of the fresh PD fluid to make sure that it has been mixed correctly, e.g., if an online PD fluid source is connected instead to one of the reusable PD fluid lines 24a to 24c. Conductivity sensor 74 may alternatively or additionally be used to detect the conductivity of the used PD fluid to assess treatment effectiveness and/or to look for patient disease, such as peritonitis. A temperature sensor 58b is located near conductivity sensor 74, so that the conductivity reading from the sensor may be temperature compensated.

A further difference with system 10b is the provision of three-way valves 132a and 132b, each under the control of control unit 50. Three-way valves 132a and 132b toggle back and forth between allowing fresh or used PD fluid flow in one direction or a second direction. Three-way valve 132a is toggled between allowing (i) fresh or used dialysis fluid to flow between piston pump 142 and patient cycler connector 30a (connected to disposable patient line 104) or (ii) PD fluid for priming or heat cleaning, such as heated fresh PD fluid to flow from valve 132a, through a reusable priming/heat cleaning line 34f, drain valve 32g, conductivity sensor 60, reusable drain line 34d (connected to disposable drain line 106 for priming) to a house or container drain for priming or in the same and/or other direction for heat cleaning. Three-way valve 132b is toggled between allowing (i) fresh or used dialysis fluid to flow between reusable pumping line 34b and patient cycler connector 30a (connected to disposable patient line 104) or (ii) air, PD fluid or a mixture thereof for priming, treatment or heat cleaning to flow from air trap 44, through reusable vent line 34e, a portion of pumping line 34b, and three-way valve 132b as discussed above through reusable drain line 34d to drain cycler connector 30b (connected to disposable drain line 106).

Still another difference with system 10b is that after disconnecting PD fluid containers 102a to 102c after treatment for heat cleaning, line connectors 26a to 26c are instead plugged into heat cleaning connectors or ports 62a to 62c for creating a closed heat cleaning loop. Ports 62a to 62c in the illustrated embodiment are each protected by a cover 64, e.g., hinged to cycler 20b, which is moved out of the way so that line connectors 26a to 26c may be connected to or plugged into heat cleaning connectors or ports 62a to 62c. Heat cleaning connectors or ports 62a to 62c may either be self-closing, e.g., spring-closed, or suitably sealed closed via covers 64. Heat cleaning connectors or ports 62a to 62c as illustrated are fluidly connected to a second heat cleaning line 34g.

For heat cleaning to create a closed heat cleaning loop, patient cycler connector 30a and drain cycler connector 30b are each provided with a recirculation cap 66, which closes sealingly against connectors 30a and 30b during heat cleaning to redirect heat cleaning fluid flowing through reusable lines 34c and 34d back into second heat cleaning line 34g (or redirect heat cleaning fluid flowing through second heat cleaning line 34g back into reusable lines 34c and 34d. Recirculation caps 66 include or define an internal fluid lumen or pathway 68 that, when closed against connectors 30a and 30b, communicates fluidly with both second heat cleaning line 34g and either reusable line 34c or reusable line 34d. The flow during disinfection/sterilization of system 10b will have many alternatives as all lines will be disinfected/sterilized. One main heat cleaning path will be, starting at pump 42, to flow out through reusable priming/heat cleaning line 34f and reusable drain line 34d drain to drain connector 30b, then passing patient connector 30a via reusable line 34g, out through heat cleaning connectors or ports 62a to 62c and back in through heater 36 and air trap 44 to pump 42.

With the heat cleaning loop closed as just described, control unit 50 performs a heat cleaning (e.g., heat disinfection or heat sterilization) sequence as described above, e.g., using heated fresh PD fluid, pumping in multiple directions, and toggling valves as needed. Three-way valves 132a and 132b in an embodiment are toggled back and forth to force heat cleaning fluid to flow in each of the alternative pathways. The heat cleaning sequence for system 10b lasts until a sufficient heat cleaning dose (e.g., AO dose) is provided to properly sterilize each of the lines forming the closed heat cleaning loop provided for cycler 10b.

Figure 3:
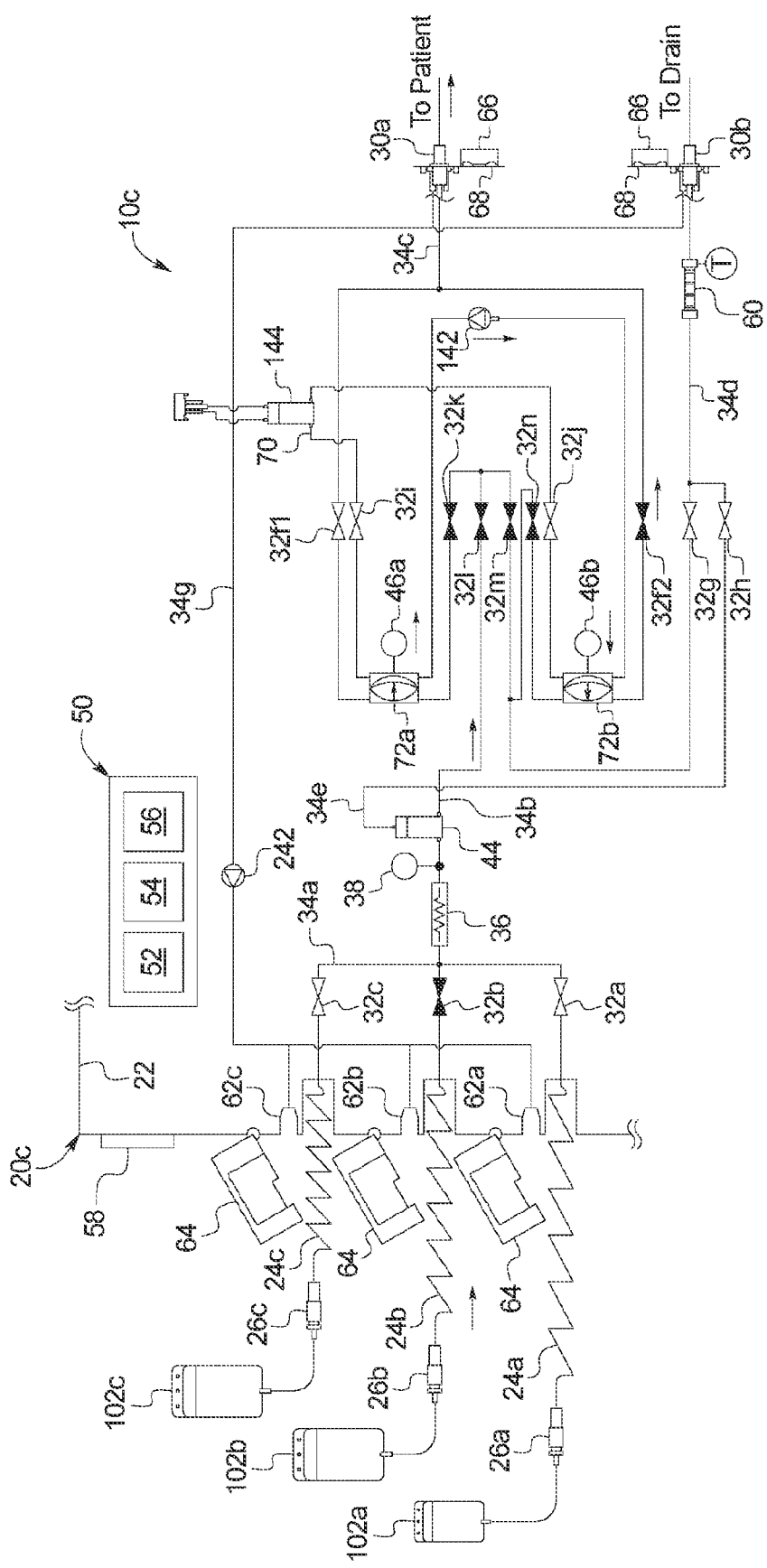
FIG. 3 is a schematic view of a third embodiment of an APD cycler and associated system using heat cleaning of the present disclosure.

Referring now to FIG. 3, another alternative APD system 10c and associated methodology of the present disclosure includes an APD machine or cycler 20c. System 10c includes many of the same components as systems 10a and 10b, which are numbered the same, which may or may not be described in connection with system 10c, but which in any case include all of the structure, functionality and alternatives discussed in connection with systems 10a and 10b. In particular, cycler 20c includes a housing 22 holding PD fluid valves 32a to 32c, reusable inlet line 34a, inline heater 36, at least one temperature sensor 38, air trap 44, reusable pumping line 34b, pressure sensors 46a and 46b, reusable patient line 34c, reusable drain line 34d, reusable vent line 34e, reusable heat cleaning line 34g, drain valve 32g, vent valve 32h, control unit 50, conductivity sensor 60 along reusable drain line 34d, and user interface 58.

Cycler 20c also includes reusable PD fluid lines 24a to 24c extending respectively to reusable line connectors 26a to 26c. Reusable patient cycler connector 30a and reusable drain cycler connector 30b are also provided. Cycler 20c of system 10c forms a closed heat cleaning loop in the same manner as cycler 10b of system 10b, using heat cleaning connectors or ports 62a to 62c and moveable covers 64 for connecting reusable PD fluid lines 24a to 24c via reusable line connectors 26a to 26c as discussed above for system 10b. Cycler 20c also provides recirculation caps 66 having internal fluid lumens or pathways for connecting to and closing reusable patient cycler connector 30a and reusable drain cycler connector 30b for heat cleaning as described for system 10b.

Cycler 20c of system 10c also includes highly inherently accurate piston or membrane pump 142 under control of control unit 50, as described above for cycler 10b of system 10b. Piston pump 142 like all pumps herein includes a body that accepts fresh or used dialysis fluid and does not operate with a disposable component. Piston pump 142 may require a flush flow of a fluid, such as reverse osmosis ("RO") water during treatment for lubrication (although a flush flow may not be needed since piston pump 142 is pumping RO water or similar). Cycler 20c as described provides a source of such RO water. In particular, cycler 20c separates the internal reusable lines or tube PD fluid lines and operating fluid lines, wherein the operating fluid lines are filled with a different operating fluid, e.g., reverse osmosis ("RO") water. Although not illustrated, operating fluid loop 70 (discussed below) that includes piston pump 142 is in one embodiment arranged to run through the flush flow ports of piston pump 142 and from the outlet flush flow port into in inlet of piston pump 142. Such arrangement likely reduces the amount of tubing needed for the flush flow and provides a more than adequate rate of flush flow.

The PD fluid lines and operating fluid lines are separated by flexible membranes provided within a pair of balance chambers 72a and 72b. Operating fluid (e.g., RO water) drives one side of each of balance chambers 72a and 72b in an operating fluid loop 70 that includes piston pump 142 and a storage chamber 144 for holding operating fluid (e.g., RO water), which ensures that there is enough operating fluid for each stroke of balance chambers 72a and 72b. Operating fluid loop 70 also includes operating fluid valves 32i and 32j under control of control unit 50, which are sequenced to stroke balance chambers 72a and 72b. Control unit 50 causes valves 32i and 32j to be closed during treatment to lock the operating fluid in place, making the operating side fluidically stiff. Valves 32i and 32j may be opened during the heat cleaning phase for circulation if it is desired to let some heat reach the operating side. Valves 32i and 32j may also be opened to let new operating fluid into piston pump 142 to compensate for any inherent leak flow between the piston and the cylinder of piston pump 142.

In each stroke of balance chambers 72a and 72b, RO pump 142 (i) pulls RO water from one balance chamber 72a or 72b, causing a like volume of fresh or used dialysis fluid to enter that balance chamber on the other side of the flexible membrane and (ii) delivers that RO water to the other balance chamber 72a or 72b, causing a like volume of fresh or used dialysis fluid to exit that balance chamber on the other side of the flexible membrane. Balance chambers 72a and 72b provide an additional layer of accuracy in case piston pump 142 becomes inaccurate for some reason. That is, the volume of balance chamber 72a or 72b is known, so each time they are stroked it can be assumed by control unit that the chamber volume of fresh dialysis fluid is delivered to balance chamber or used dialysis fluid is removed from the patient. Counting the strokes of balance chambers 72a or 72b accordingly allows control unit 50 to accumulate a total fresh and used PD fluid delivered. That amount may be compared to the fresh and used PD fluid totals calculated by control unit 50 counting known volume pumping strokes of RO piston pump 142.

In the illustrated embodiment, control unit 50 during treatment closes operating fluid valves 32i and 32j and causes piston pump 142 to pump in opposite directions to either (i) pull RO water from balance chamber 72a and push same to balance chamber 72b or (ii) pull RO water from balance chamber 72b and push same to balance chamber 72a. During non-treatment, control unit 50 may open one or both of operating fluid valves 32i and 32j (or toggle the valves opened and closed) for various reasons discussed above and additionally for fresh flush flow of RO at piston pump 142.

On the treatment fluid side, cycler 20c includes a pair of patient valves 32f1 and 32f2, each under control of control unit 50. Patient valve 32f1 either allows fresh PD fluid to flow from an output stroke of balance chamber 72a to the patient via reusable patient line 34c or used PD fluid to flow from the patient via reusable patient line 34c to balance chamber 72a during an intake stroke. Patient valve 32f2 likewise either allows fresh PD fluid to flow from an output stroke of balance chamber 72b to the patient via reusable patient line 34c or used PD fluid to flow from the patient via reusable patient line 34c to balance chamber 72b during an intake stroke.

On the treatment fluid side, cycler 20c also includes plural supply and/or drain outlet valves 32k to 32n, each under control of control unit 50. Supply and drain outlet valve 32k either allows fresh PD fluid to flow via reusable pumping line 34b to balance chamber 72a during an intake stroke or used PD fluid to flow from balance chamber 72a to drain via drain line 34d during an output stroke. Supply valve 32l is used to allow fresh PD fluid to flow via reusable pumping line 34b to either balance chamber 72a or balance chamber 72b during an intake stroke. Supply valve 32m allows, during a fresh PD fluid intake stroke, fresh PD fluid to flow via reusable pumping line 34b to balance chamber 72b, and during a used PD fluid outflow stroke, allows used PD fluid to flow from balance chamber 72a to drain via reusable drain cycler connector 30b. Supply and drain outlet valve 32n either allows fresh PD fluid to flow via reusable pumping line 34b to balance chamber 72b during an intake stroke or used PD fluid to flow from balance chamber 72b to drain via drain line 34d during an output stroke. Control unit 50 also sequences supply and/or drain outlet valves 32k to 32n during heat cleaning to direct fresh, heated PD fluid in a desired manner during the sequence.

Cycler 20c provides various advantages including enabling pressure sensors 46a and 46b to be positioned along the operating fluid loop 70, which means that if a fluid leak involving the pressure sensors occurs, the leak involves RO water, not dialysis fluid. Pressure sensors 46a and 46b nevertheless provide accurate positive and negative PD fluid pressure readings, wherein PD fluid pressure is accurately transferred across the flexible membranes of balance chambers 72a and 72b. Also, piston pump 142 pumps RO water instead of fresh or used PD fluid, which may lessen wear and increase component life (e.g., of pressure sensors 46a and 46b) due at least in part because piston pump 142 does not need to be subjected to heated or chemical heat cleaning fluid. Placing the components in the operating fluid loop 70 makes cycler 20c well suited for higher temperatures and cleaning times associated with sterilization versus heat cleaning discussed above. Moreover, as mentioned above, operating fluid loop 70 and storage chamber 144 provide a ready supply of flush flow fluid for piston pump 142.

After treatment, with the heat cleaning loop closed as described in connection with cycler 20b (PD fluid lines 24a to 24c connected to the cycler and recirculation caps 66 closed), control unit 50 performs a heat cleaning (e.g., heat disinfection or heat sterilization) sequence for cycler 20c using, e.g., heated fresh PD fluid, pumping in multiple directions, and toggling valves as needed. Cycler 20c may provide an additional heat cleaning pump 242 under control of control unit 50, e.g., a less accurate gear pump, centrifugal or other type of pump, along reusable heat cleaning line 34g if needed. The heat cleaning (e.g., cleaning activity) sequence for system 10c lasts until a sufficient heat cleaning dose is provided to properly sterilize each of the treatment fluid lines forming the closed heat cleaning loop provided for cycler 10c. Again, operating fluid loop 70 does not need to be disinfected.

Figure 4:
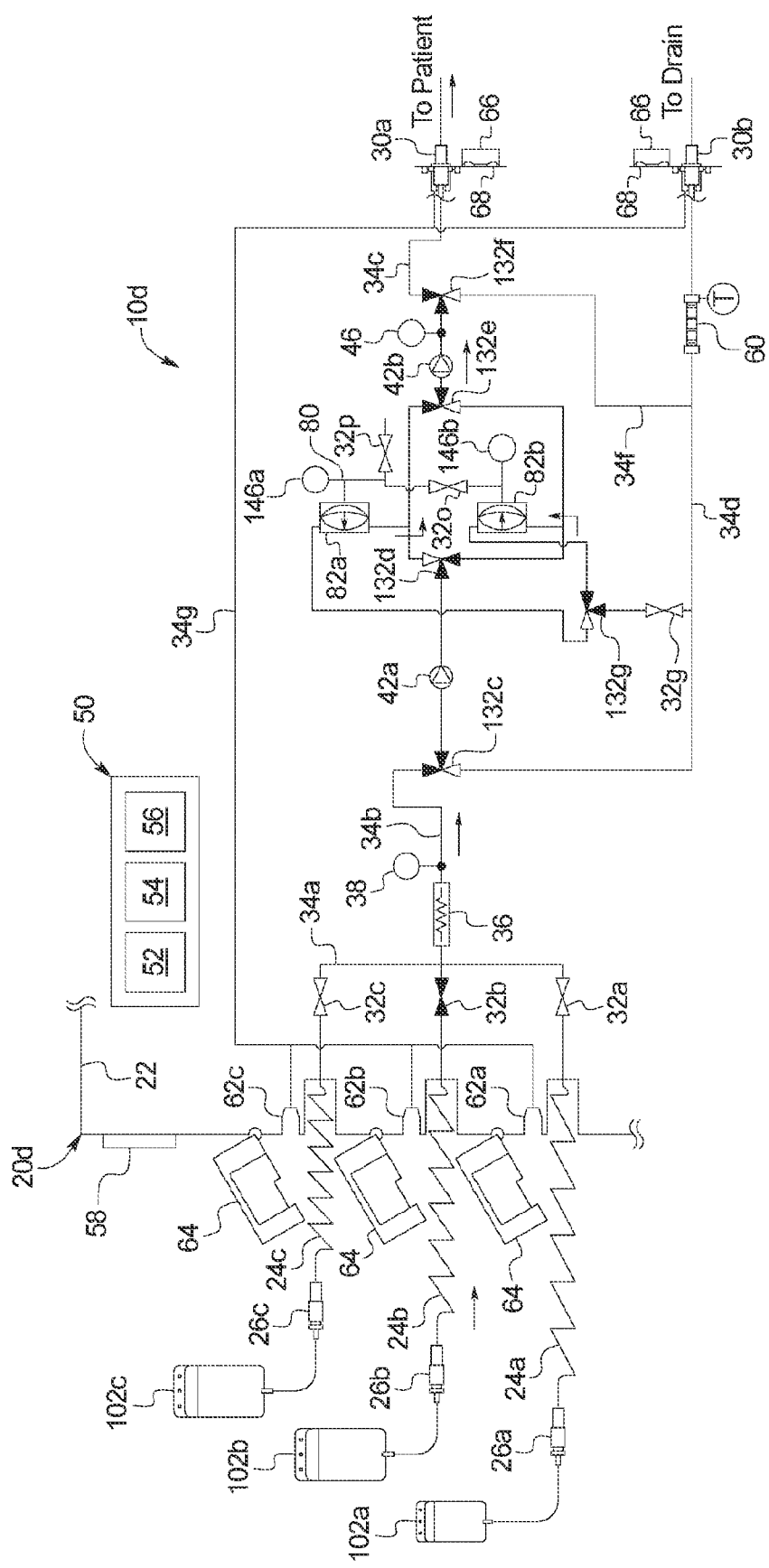
FIG. 4 is a schematic view of a fourth embodiment of an APD cycler and associated system using heat cleaning of the present disclosure.

Referring now to FIG. 4, another alternative APD system 10d and associated methodology of the present disclosure includes an APD machine or cycler 20d. System 10d includes many of the same components as systems 10a to 10c, which are numbered the same, which may or may not be described in connection with system 10d, but which in any case include all of the structure, functionality and alternatives discussed in connection with systems 10a to 10c. In particular, cycler 20d includes a housing 22 holding PD fluid valves 32a to 32c, reusable inlet line 34a, inline heater 36, at least one temperature sensor 38, reusable pumping line 34b, pressure sensor 46, reusable patient line 34c, reusable used PD fluid line 34d, reusable heat cleaning line 34g, recirculation valve 32g, conductivity sensor 60 located along reusable used PD fluid line 34d, control unit 50 and user interface 58.

Cycler 20d also includes reusable PD fluid lines 24a to 24c extending respectively to reusable line connectors 26a to 26c. Reusable patient cycler connector 30a and reusable drain cycler connector 30b are also provided. Cycler 20d of system 10d forms a closed heat cleaning loop in the same manner as cyclers 20b and 20c of systems 10b and 10c, using heat cleaning connectors or ports 62a to 62c and moveable, e.g., hinged, covers 64 for connecting reusable PD fluid lines 24a to 24c via reusable line connectors 26a to 26c as discussed above for systems 10b and 10c. Cycler 20d also provides recirculation caps 66 having internal fluid lumens or pathways for connecting to and fluidly closing reusable patient cycler connector 30a and reusable drain cycler connector 30b for heat cleaning as described for systems 10b and 10c.

Cycler 20d of system 10d is also like cycler 20a of system 10a in that a less accurate gear, centrifugal or other type of pump may be used, here two gear or other pumps 42a and 42b each under control of control unit 50. Cycler 20d also provides volumetric chambers 82a and 82b having flexible membranes similar to the balancing chambers 72a and 72b of cycler 20c. But in FIG. 4, fresh or used PD fluid is delivered and removed from one side of the volumetric chamber membranes, while air is moved back and forth on the other sides of the membranes, as opposed to the dual fluids of the third primary embodiment. In one embodiment during a fill phase, gear pump 42a is used to pull fresh PD fluid from at least one of the PD fluid containers 102a to 102c and deliver the fluid to one of the volumetric chambers 82a and 82b, while gear pump 42b is delivers fresh fluid from the other of the volumetric chambers 82a and 82b to the patient. During a drain phase, gear pump 42b is instead used to pull used PD fluid from the patient and deliver this fluid to one of the volumetric chambers 82a and 82b, while gear pump 42a delivers used PD fluid from the other of the volumetric chambers 82a and 82b to drain via drain port 30b.

The other sides of the membranes in volumetric chambers 82a and 82b are sequentially filled with air and have air purged from the chambers. The air sides of volumetric chambers 82a and 82b communicate pneumatically with an air circuit 80. Air circuit 80 in the illustrated embodiment includes two air valves 32o and 32p, each under control of control unit 50.

Air valves 32o and 32p are closed during treatment in one embodiment, locking volumes of air in volumetric chambers 82a and 82b (different locked volumes are possible since the volumes depend on where the membrane is located when valves 32o or 32p close). When one of chambers 82a or 82b is filled with fresh or used PD fluid, the corresponding pressure sensor 146a or 146b measures the pressure raise. Control unit 50 of system 10d knows the pressure profile and stops the filling of PD fluid at a predetermined pressure value. The flowrate may be lower at the end of a chamber fill stroke to more easily detect a switching point and to minimize risk of high pressures in chambers 82a or 82b during operation. Both air valves 32o and 32p may be opened during heat cleaning, for example, to allow the PD fluid sides of volumetric chambers 82a and 82b to both be filled with, e.g., heated fresh PD heat cleaning fluid. Vent valve 32p may be opened while air valve 32o is closed to move the membrane in volumetric chamber 82a without correspondingly moving the membrane of volumetric chamber 82b if desired.

In the illustrated embodiment, cycler 20d includes a plurality of three-way valves under control of control unit 50, which are to control PD fluid and heat cleaning fluid flow. A first three-way valve 132c is provided upstream of gear or other type of pump 42a and is dedicated to direct fresh (from heater 36) PD fluid to, or used (from the patient) PD fluid from, volumetric chambers 82a or 82b (depending on phase). A second three-way valve 132d is provided downstream from gear pump 42a and is also dedicated to direct fresh PD fluid to, or used PD fluid from, volumetric chambers 82a and 82b. A third three-way valve 132e is provided upstream of gear pump 42b and is used for directing fresh PD fluid from or used PD fluid to, the volumetric chambers 82a and 82b. A fourth three-way valve 132f is provided downstream of gear pump 42b and is also dedicated to direct fresh PD fluid to, and used PD fluid from, the patient and to direct air or/and fresh PD fluid to drain during priming or an air removal phase. A fifth three-way valve 132g is provided for example to cycle back and forth between first and second volumetric chambers 82a and 82b during heat cleaning.

In the illustrated embodiment, pressure sensor 46 is located between downstream pump 42b and reusable patient cycler connector 30a to output to control unit 50 to control patent pressure as described herein. Additionally, air pressure sensors 146a and 146b are provided for sensing the air pressure on the "dry" side of each of the membranes of the first and second volumetric chambers 82a and 82b, respectively, which reflects fresh and used PD fluid pressures on the other sides of the membranes. Control unit 50 may compare the readings from pressure sensors 146a and 146b and pressure sensor 46, e.g., at the startup of treatment, to confirm that the pressure sensors are measuring the same pressures. If not, control unit 50 may determine that one of pressure sensors 146a, 146b or 46 has drifted and cause a service notice to be posted on user interface 58 of APD cycler 20d.

After treatment, with the heat cleaning loop closed as described in connection with cycler 20b (PD fluid lines 24a to 24c connected to the cycler and recirculation caps 66 closed), control unit 50 performs a heat cleaning (e.g., heat disinfection or heat sterilization) sequence for cycler 20d using, e.g., heated fresh PD fluid, pumping in multiple directions, and toggling valves as needed. Cycler 20d may toggle each three-way valve 132c to 132g multiple times during heat cleaning to ensure that heat cleaning fluid contacts each pathway of the closed heat cleaning loop of the cycler. The heat cleaning (e.g., heat disinfection or heat sterilization) sequence for system 10d lasts until a sufficient heat cleaning dose (e.g., AO dose) is provided to properly sterilize each of the treatment fluid lines forming the closed heat cleaning loop provided for cycler 10d.

Figure 5:
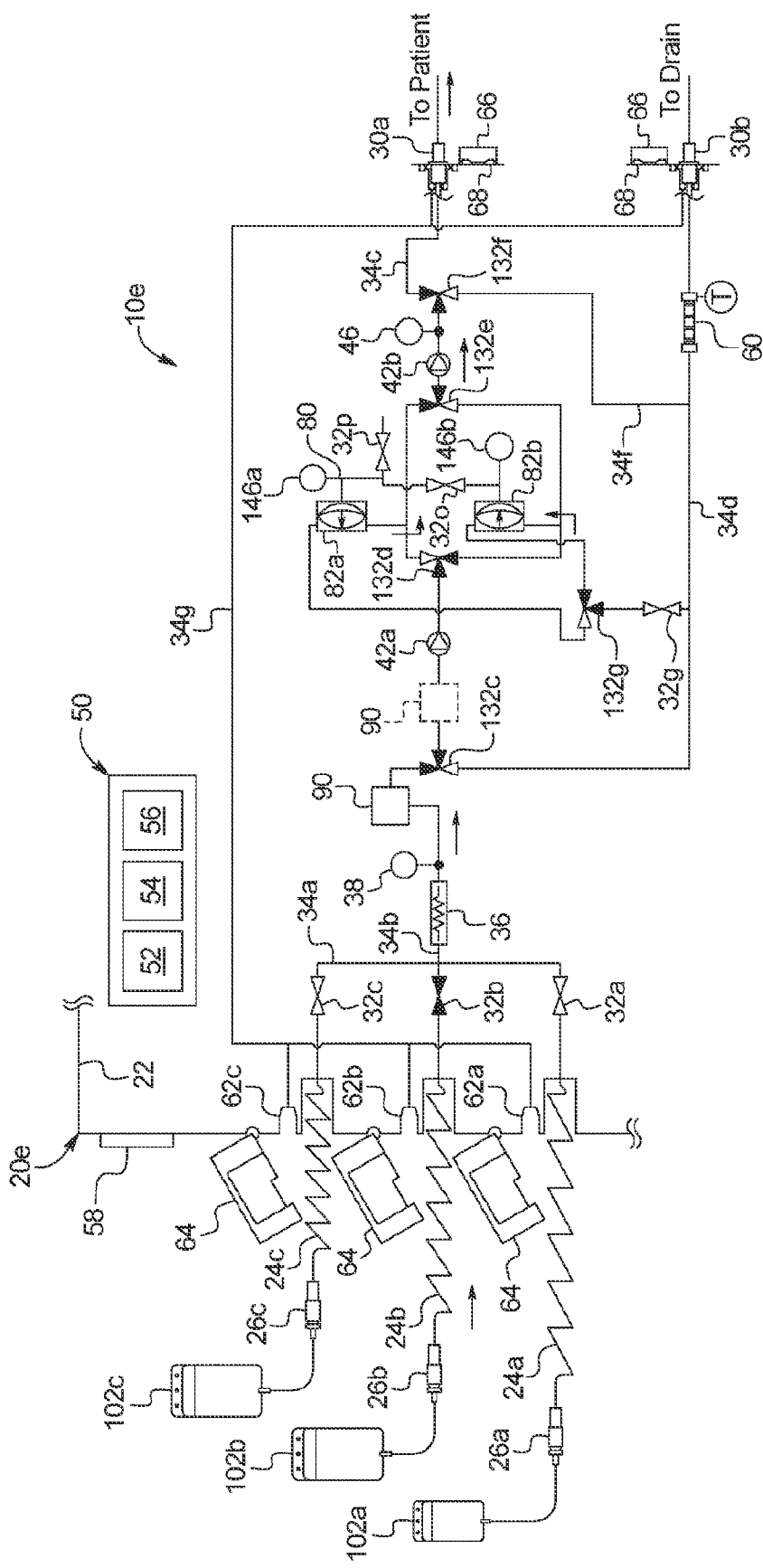
FIG. 5 is a schematic view of a fifth embodiment of an APD cycler and associated system using heat cleaning of the present disclosure.

Referring now to FIG. 5, another alternative APD system 10e and associated methodology of the present disclosure includes an APD machine or cycler 20e including a housing 22. System 10e includes all structure, functionality and alternatives described above for cycler 20d of system 10d, including all valve and pump sequencing for the treatment and heat cleaning procedures (including connections for closing the heat cleaning loop) described for cycler 20d. Cycler 20e adds a flow sensor 90 outputting to control unit 50 for tracking the volume of fresh and used PD fluid delivered to and removed from the patient. It is a goal of cycler 20d of system 10e to rely on the accuracy of volumetric chambers 82a and 82b on a per stroke basis and for control unit 50 to count the number of strokes to determine an overall volume of fresh and used PD fluid delivered. However, if the per stroke accuracy of volumetric chambers 82a and 82b is found to be not accurate enough, then additional flow sensor 90 may be used, wherein its output is integrated by control unit 50 over time to determine overall fresh and used PD volumes delivered and a resulting patient fluid removal (e.g., UF).

In FIG. 5, flow sensor 90 is placed in alternative locations. If flow sensor is a single direction flow sensor, then it may be placed upstream of three-way valve 132c so that flow sensor 90 only sees fresh PD fluid, wherein no proteins, etc., from the patient build-up on its surfaces, which helps to maintain accuracy. Here, it is contemplated for control unit 50 to monitor the flow of fresh PD fluid, which is tied to the movement of the membranes of volumetric chambers 82a and 82b. A certain membrane movement in a patient filling phase is correlated to certain fresh PD fluid flowrate as measured by flow sensor 90. The same membrane movement in a patient draining phase, where flow sensor 90 is not used, may then be assumed to yield the same used PD flowrate (or an extrapolated flowrate may be correlated to a different membrane movement). In any case, drain flow can be determined based on the measurements performed during the fill phase. If flow sensor 90 is a bidirectional flow sensor, then it may be placed downstream of three-way valve 132c (dashed lines) so that the flow sensor can measure fresh and used PD flow in multiple directions.

Figure 6:
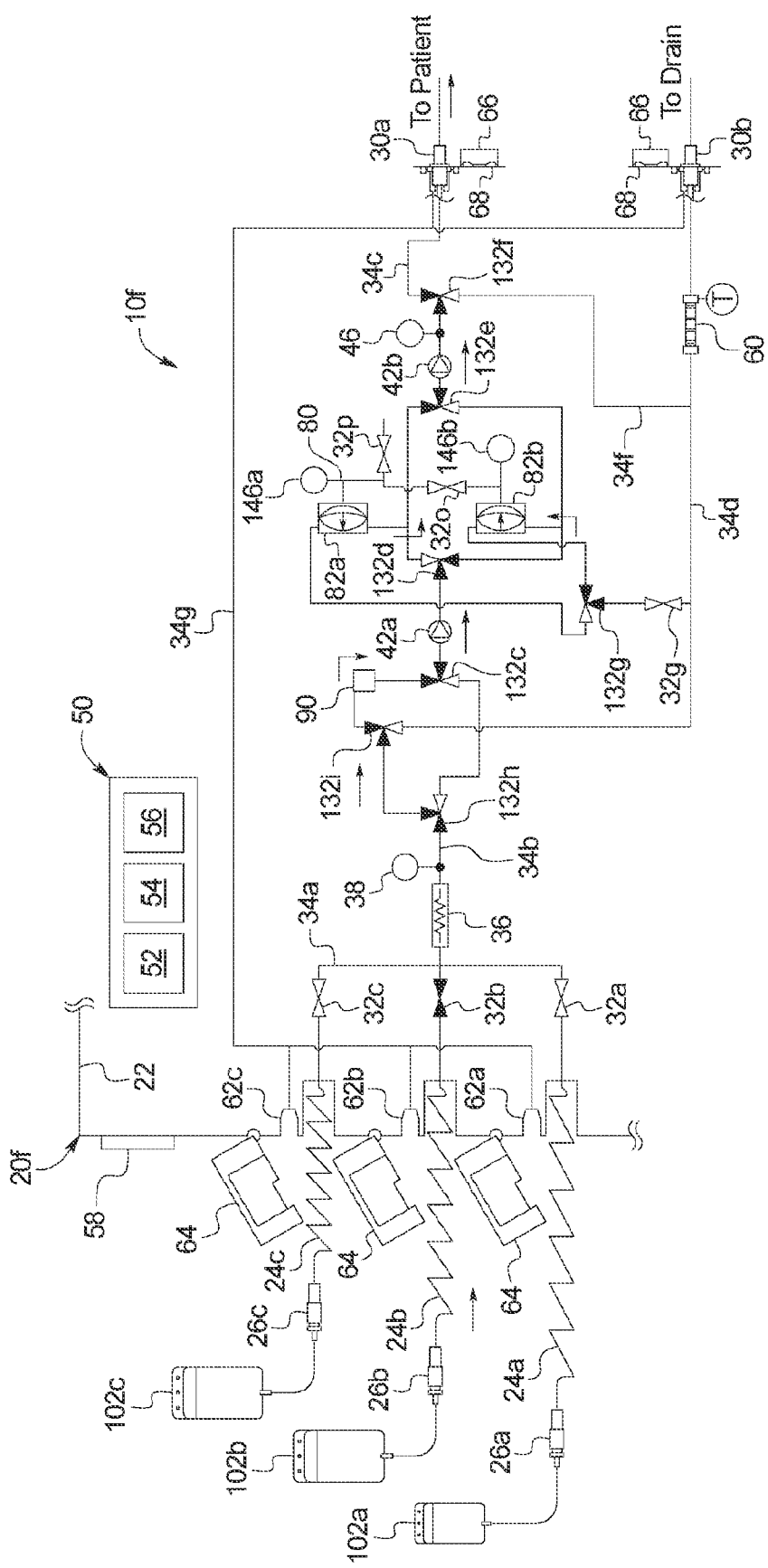
FIG. 6 is a schematic view of a sixth embodiment of an APD cycler and associated system using heat cleaning of the present disclosure.

Referring now to FIG. 6, a further alternative APD system 10f and associated methodology of the present disclosure includes an APD machine or cycler 20f including a housing 22. System 10f includes all structure, functionality and alternatives described above for cycler 20d, including all valve and pump sequencing for the treatment and heat cleaning procedures (including connections for closing the heat cleaning loop) described for cycler 20d. System 10f also includes flowmeter 90 outputting to control unit 50, which is provided again for tracking the volume of fresh and used PD fluid delivered to and removed from the patient. Cycler 20f adds additional three-way valves 132h and 132i and associated fluid lines so that PD fluid may flow through flow sensor 90 in the same direction regardless of whether the PD fluid is fresh or used. Cycler 20f of system 10f expands the number of different flow sensors 90 that may be used because not all flow sensors are bidirectional.

A seventh embodiment, not illustrated, may use any one of the same general flow paths as cyclers 20d to 20f of systems 10d to 10f, but wherein the driving force is air, which may be provided from positive and negative tanks that are pressurized via a pneumatic pump under the control of control unit 50. The tanks may feed positive and negative pneumatic pressure regulators, respectively, which provide regulated positive and negative pneumatic pressure to, e.g., electronically controlled, pneumatic solenoid valves, which drive membrane fluid pumps and valves. The benefit is that the membrane fluid pumps are reusable, which may be calibrated to high accuracy in production. Also, the membrane pump chambers may be relatively large, resulting in the actuation of the membrane fluid valves operable with the membrane fluid pump being less frequent, which in turn should improve reliability.

It should be understood that various changes and modifications to the presently preferred embodiments described herein will be apparent to those skilled in the art. It is therefore intended that such changes and modifications be covered by the appended claims. For example, while heat cleaning (e.g., heat disinfection or heat sterilization) is disclosed, chemical cleaning, e.g., citric acid, may be provided alternatively or in addition to heat cleaning. There may be chemical benefits to using used dialysis fluid as a cleaning fluid. Other types of disinfection, e.g., ultraviolet light, may be used additionally. Also, while system 10c of FIG. 3 is described as using RO water for its process fluid, air or a different process fluid could be used alternatively. Further, while systems 10d to 10f of FIGS. 4 to 6 are described as using air for its compressible fluid, other gases or compressible fluids may be used alternatively.

The invention is claimed as follows:

1. A peritoneal dialysis ("PD") system comprising:
a housing;
a dialysis fluid pump housed by the housing and including a reusable pump body that accepts PD fluid for pumping;
a dialysis fluid inline heater housed by the housing and including a reusable heater body that accepts PD fluid for heating;
a patient line connector presented by the housing and configured to connect to a disposable patient line, the patient line connector in combination with the disposable patient line being configured to provide PD fluid from the dialysis fluid pump to a patient for a PD treatment;
a drain line connector presented by the housing and configured to connect to a disposable drain line for the PD treatment, the drain line connector in combination with the disposable drain line being configured to provide used PD fluid from the patient to a drain for the PD treatment;
a first reusable PD fluid line extending from the housing and including a first connector configured to (i) mate with the patient line connector for a heat cleaning sequence, and (ii) mate with a first PD fluid container for the PD treatment;
a second reusable PD fluid line extending from the housing and including a second connector configured to (i) mate with the drain line connector for the heat cleaning sequence, and (ii) mate with a second PD fluid container for the PD treatment; and
a control unit configured to run the heat cleaning sequence after the PD treatment, wherein the first connector of the first reusable PD fluid line is disconnected from the first PD fluid container and mated with the patient line connector, the second connector of the second reusable PD fluid line is disconnected from the second PD fluid container and mated with the drain line connector, and the dialysis fluid pump and the dialysis fluid inline heater are actuated during the heat cleaning sequence.

2. The PD system of claim 1, further comprising an additional connector presented by the housing, a third reusable PD fluid line extending from the housing, and a third connector configured to mate with the additional connector for the heat cleaning sequence.

3. The PD system of claim 2, further comprising a fourth fluid line including a fourth connector configured to mate with the additional connector during the PD treatment.

4. The PD system of claim 3, wherein the fourth fluid line is configured to be used to provide additional PD fluid for the PD treatment or is configured to be used as a location to store an effluent sample.

5. The PD system of claim 1, further comprising the first and second PD fluid containers configured to connect to the first and second connectors, respectively.

6. The PD system of claim 1, wherein the first and second connectors are different from each other.

7. The PD system of claim 1, further comprising the disposable patient line configured to connect to the patient line connector and the disposable drain line configured to connect to the drain line connector.

8. The PD system of claim 1, wherein at least one of the first and second reusable PD fluid lines is provided with a lid that is opened and closed to disconnect and connect, respectively, the first connector from and to the patient line connector or the second connector from and to the drain line connector.

9. The PD system of claim 1, wherein the control unit is configured to cause (i) the dialysis fluid inline heater to heat the PD fluid accepted by the reusable heater body to at least 70° C. or at least 120° C. for a sterilization level of heat cleaning and (ii) the dialysis fluid pump to recirculate the heated PD fluid during the heat cleaning sequence.

10. The PD system of claim 1, wherein the dialysis fluid pump is a piston pump, a gear pump, or a membrane pump.

* * * * *